(12) United States Patent
Hirschberg et al.

(10) Patent No.: US 9,453,237 B2
(45) Date of Patent: Sep. 27, 2016

(54) ORGANISM WITH ALTERED CAROTENOID CONTENT AND METHOD OF PRODUCING SAME

(75) Inventors: Joseph Hirschberg, Jerusalem (IL); Dani Zamir, Gedera (IL)

(73) Assignee: Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 411 days.

(21) Appl. No.: 13/582,945

(22) PCT Filed: Mar. 9, 2011

(86) PCT No.: PCT/IL2011/000225
§ 371 (c)(1),
(2), (4) Date: Oct. 23, 2012

(87) PCT Pub. No.: WO2011/111041
PCT Pub. Date: Sep. 15, 2011

(65) Prior Publication Data
US 2013/0036518 A1  Feb. 7, 2013

Related U.S. Application Data

(60) Provisional application No. 61/312,082, filed on Mar. 9, 2010.

(51) Int. Cl.
| | | |
|---|---|---|
| *A01H 5/00* | (2006.01) | |
| *A01H 5/02* | (2006.01) | |
| *A01H 5/08* | (2006.01) | |
| *C12N 5/10* | (2006.01) | |
| *C12N 15/82* | (2006.01) | |
| *C07K 14/415* | (2006.01) | |

(52) U.S. Cl.
CPC ........... *C12N 15/825* (2013.01); *C07K 14/415* (2013.01)

(58) Field of Classification Search
None
See application file for complete search history.

(56) References Cited

U.S. PATENT DOCUMENTS

| | | |
|---|---|---|
| 4,987,071 A | 1/1991 | Cech |
| 6,326,174 B1 | 12/2001 | Joyce |
| 7,705,215 B1 * | 4/2010 | Adams ..................... A01H 4/00 435/189 |

OTHER PUBLICATIONS

Li et al., 2007, Plant Physiology 144: 1181-1189.*
Chen et al., 2010, Plant Physiology 153: 66-79.*
Sandmann, 2009, Archives of Biochemistry and Biophysics 483: 169-174.*
Giuliano et al., 2008, Trends in Biotechnology 26: 139-145.*
Viney and Thompson, 2008, International Journal for Parasitology 38: 43-47.*
Roth et al., Virus Research 102: 97-108.*
Schnable et al., GenBank Accession No. NM_001139248.1, Nov. 14, 2008.*
Schultes and and Bartel, 2000, Science 289: 448-452.*
Small, 2007, Current Opinion in Biotechnology 18: 148-153.*
Zybailov et al., 2008, PLoS ONE. 2008; 3(4): e1994.*
Dornelas and Dornelas, 2005, Brazilian Journal of Plant Physiology 17: 335-343.*
Fraser et al., 2009, Archives of Biochemistry and Biophysics 483: 196-204.*
Fantini et al., "Dissection of Tomato Lycopene Biosynthesis through Virus-Induced Gene Silencing", Plant Physiology, 163:986-998 (Oct. 2013).
Schwab et al., "Highly Specific Gene Silencing by Artificial MicroRNAs in Arabidopsis", The Plant Cell, 18:1121-1133 (May 2006).
Matthews et al., (2003) Maize phytoene desaturase and zeta-carotene desaturase catalyse a poly-Z desaturation pathway: implications for genetic engineering of carotenoid content among cereal crops. J Exp Bot 54(391): 2215-30.
Aoki, Koh et al., "Large-scale analysis of full-length cDNAs from the tomato (*Solanum lycopersicum*) cultivar Micro-Tom, a reference system for the Solanaceae genomics", BMC Genomics, 11(3):210 (2010).
Aust, O. et al., "Supplementation with tomato-based products increases lycopene, phytofluene, and phytoene levels in human serum and protects against UV-light-induced erythema", Int J Vitam Nutr Res, 75(1):54-60 (2005).
Ben-Amotz, Ami et al., "Massive accumulation of phytoene induced by norflurazon in Dunaliella bardawil (Chlorophyceae) prevents recovery from photoinhibition1", J Phycol, 23:176-181 (1987).
Bernatzky, R. and Tanksley, S., "Methods for detection of single or low copy sequences in tomato on southern blots", Plant Mol Biol Reporter, 4(1):37-41 (1986).
Campbell, Jessica K. et al., "Phytoene, Phytofluene, and Lycopene from Tomato Powder Differentially Accumulate in Tissues of Male Fisher 344 Rats", Nutr Res, 27(12):794-801 (2007).
Casanitjana-Martinez, Eva et al., "Root-specific CLE19 overexpression and the sol1/2 suppressors implicate a CLV-like pathway in the control of Arabidopsis root meristem maintenance", Curr Biol, 13(16):1435-1441 (2003).

(Continued)

*Primary Examiner* — David T Fox
*Assistant Examiner* — Bratislav Stankovic
(74) *Attorney, Agent, or Firm* — Rodney J. Fuller; Booth Udall Fuller, PLC

(57) ABSTRACT

The present invention relates to means and methods for modifying the expression of a component in the carotenoid biosynthetic pathway to modify the production of carotenoid towards accumulation of at least one of phytoene, phytofluene, zeta carotene or combinations thereof. The present invention further relates to genetically altered organisms having elevated content of these carotenoids. The present invention further relates to genetically altered organisms having elevated content of these carotenoids, particularly in chromoplast-containing cells.

12 Claims, 13 Drawing Sheets

(56) References Cited

OTHER PUBLICATIONS

Chen, Yu et al., "Isolation and characterization of the Z-ISO gene encoding a missing component of carotenoid biosynthesis in plants", Plant Physiol, 153(1):66-79 (2010).

Cooper, Dale A., "Carotenoids in health and disease: recent scientific evaluations, research recommendations and the consumer", J Nutr, 134(1):221S-224S (2004).

Cunningham, Francis X. Jr. et al., "Cloning and functional expression in *Escherichia coli* of a cyanobacterial gene for lycopene cyclase, the enzyme that catalyzes the biosynthesis of beta-carotene", FEBS Lett, 328(1-2):130-138 (1993).

Cunningham, Francis X. Jr. et al., "Molecular structure and enzymatic function of lycopene cyclase from the cyanobacterium *Synechococcus* sp strain PCC7942", Plant Cell, 6(8):1107-1121 (1994).

Dellapenna, Dean, "Nutritional genomics: manipulating plant micronutrients to improve human health", Science, 285(5426):375-379 (1999).

Eckert, K. A. and Kunkel, T. A., "DNA polymerase fidelity and the polymerase chain reaction", PCR Methods and Appl,1(1):17-24 (1991).

Estornell, Leandro Hueso et al., "A multisite gateway-based toolkit for targeted gene expression and hairpin RNA silencing in tomato fruits", Plant Biotechnol J, 7(3):298-309 (2009).

Fernandez, Ana I. et al., "Flexible tools for gene expression and silencing in tomato", Plant Physiol, 151(4):1729-1740 (2009).

Fire, Andrew et al., "Potent and specific genetic interference by double-stranded RNA in Caenorhabditis elegans", Nature, 391(6669):806-811 (1998).

Galpaz, Navot et al., "Abscisic acid deficiency in the tomato mutant high-pigment 3 leading to increased plastid number and higher fruit lycopene content", Plant J, 53(5):717-730 (2008).

Guo, Su and Kemphues, Kenneth J., "par-1, a gene required for establishing polarity in C. elegans embryos, encodes a putative Ser/Thr kinase that is asymmetrically distributed", Cell, 81(4):611-620 (1995).

Holtman, C. Kay et al., "High-throughput functional analysis of the Synechococcus elongatus PCC 7942 genome", DNA Res, 12(2):103-115 (2005).

Ingelbrecht, Ivan L. W. et al., "Different 3' end regions strongly influence the level of gene expression in plant cells", Plant Cell, 1(7):671-680 (1989).

Isaacson, Tal et al., "Cloning of tangerine from tomato reveals a carotenoid isomerase essential for the production of beta-carotene and xanthophylls in plants", Plant Cell, 14(2):333-342 (2002).

Isaacson, Tal et al., "Analysis in vitro of the enzyme CRTISO establishes a poly-cis-carotenoid biosynthesis pathway in plants", Plant Physiol, 136(4):4246-4255 (2004).

Ishida, Yuji et al., "Agrobacterium-mediated transformation of maize", Nature Protoc, 2(7):1614-1621 (2007).

Khachigian, Levon M., "DNAzymes: cutting a path to a new class of therapeutics", Curr Opin Mol Ther, 4(2):119-121 (2002).

Li, Faqiang et al., "Maize Y9 encodes a product essential for 15-cis-zeta-carotene isomerization", Plant Physiol, 144(2):1181-1189 (2007).

Lichtenthaler, Hartmut K., "Chlorophylls and carotenoids, the pigments of photosynthetic biomembranes", Methods Enzymol, 148:350-382 (1987).

Lindsay, David G., "The nutritional enhancement of plant foods in Europe. 'NEODIET'", Trends in Food Sci. Technol, 11(4-5):145-151 (2000).

Lotan, Tamar and Hirschberg, Joseph, "Cloning and expression in*Escherichia coli* of the gene encoding β-C-4-oxygenase, that converts β-carotene to the ketocarotenoid canthaxanthin in Haematococcus pluvialis", FEBS Lett, 364(2):125-128 (1995).

Lu, Shan and Li, Li, "Carotenoid Metabolism: Biosynthesis, Regulation, and Beyond", J Integr Plant Biol, 50(7):778-785 (2008).

Mathews-Roth, Micheline M. and Pathak, Madhu A., "Phytoene as a protective agent against sunburn (greater than 280 nm) radiation in guinea pigs", Photochem Photobiol, 21(4):261-263 (1975).

McCallum, Claire M. et al., "Targeted screening for induced mutations", Nat Biotechnol, 18(4):455-457 (2000).

Menda, Naama et al., "In silico screening of a saturated mutation library of tomato", Plant J, 38(5):861-872 (2004).

Palombo, P. et al., "Beneficial long-term effects of combined oral/topical antioxidant treatment with the carotenoids lutein and zeaxanthin on human skin: a double-blind, placebo-controlled study", Skin Phamnacol Physiol, 20(4):199-210 (2007).

Park, Hyoungshin et al., "Identification of the carotenoid isomerase provides insight into carotenoid biosynthesis, prolamellar body formation, and photomorphogenesis", Plant Cell, 14(2):321-332 (2002).

Shaish, Aviv et al., "A carotenoid algal preparation containing phytoene and phytofluene inhibited LDL oxidation in vitro", Plant Foods Hum Nutr, 63(2):83-86 (2008).

Stahl, Wilhelm et al., "Dietary tomato paste protects against ultraviolet light-induced erythema in humans", J Nutr, 131(5):1449-1451 (2001).

Stahl, Wilhelm et al., "Lycopene-rich products and dietary photoprotection", Photochem Photobiol Sci, 5(2):238-242 (2006).

Stahl, Wilhelm and Sies, Helmut, "Antioxidant activity of carotenoids", Mol Aspects Med, 24(6):345-351 (2003).

Van Den Berg, H. et al., "The potential for the improvement of carotenoid levels in foods and the likely systemic effects", J Sci Food Agric, 80(7):880-912 (2000).

Zheng, Lei et al., "An efficient one-step site-directed and site-saturation mutagenesis protocol", Nucleic Acid Res, 10(14):32(14):e115 (2004).

ISR of PCT/IL2011/000225 Jun. 15, 2011.

Database EMBL [Online] Mar. 19, 2009 "Solanum lycopersicum cDNA, clone: LEFL2002DC06. HTC in fruit.". retrieved from EBI accession No. EMBL:AK326152 sequence.

* cited by examiner

| | | | | |
|---|---|---|---|---|
| ccccaccgag | caatctgtca | agagagcaaa | agcagagtta | aaacgtgtac | tggaggacat | 60 |
| taccatgcaa | gcatcatcac | ttcctggttc | ggctcaacca | ggcagatact | cagttgtata | 120 |
| agaatgaaca | ccgttgtcat | tatgatgtta | cttttatct | attatcttt | ccgagcaaat | 180 |
| tatttcctaa | attttgttac | tcaatttgga | gatgacttac | tttgtaatga | tataaacagg | 240 |
| tttaactaga | tacatgattc | tcagtgatca | tcggccatgg | ttagttcctc | tcctatatta | 300 |
| tctcatacct | gttatctgta | ttacttgatt | cctttactga | tagtatcatc | aaagctgcta | 360 |
| tttgaattga | aactgccaca | gggagattac | atagagttgc | ccaggaagaa | gcatggtatt | 420 |
| cagtcacccc | gactaatatc | ttgttaggaa | agaaaccctg | tggtaacttt | tgtaacacaa | 480 |
| ttacttgaat | ttcctattta | ctcatgttat | agagtagcag | aattgcttga | attctatgca | 540 |
| tgaggaatca | tcatatgcac | aaggttgatg | acgattttca | tgatggcatt | gatccatata | 600 |
| cctaatggat | cgtgagacga | ctactagagc | aaaggtatat | tgactagatt | cagtgttgtc | 660 |
| tttccatctt | ctttgtggat | ttggtagtaa | atgaaaacag | gtactgactt | gactttttat | 720 |
| atttctaaaa | tgttaaaaac | tttacaagtt | taaaatgtta | aaccttctgc | ttgtagattc | 780 |
| tcaagcaaca | ctaacaaaaa | aaaaaaaaa | aaggaaaga | aaatgtgaaa | tgcctttggc | 840 |
| tctgtcttgt | ccaatggatt | ataagctttg | gtttacttgc | tataaagaga | ctggaagcta | 900 |
| tctcaatgca | tcgatacgtt | gttttttgtt | aagagtaccc | actcctgaag | actatataca | 960 |
| tcttcccctt | acaggttagg | cctgttgccg | agaacgtggt | aagaagttgt | aaaaagaaaa | 1020 |
| gcatgtactg | ttcagagtca | tctagtgtca | tttggttagt | tggttaaact | gaatttacat | 1080 |
| gctcaactcc | cttgttttag | attctactat | ttatgtacta | tttttctttg | agttgaacg | 1140 |
| gtatgtgtcg | ttctgacttg | ttctgctgtt | ctcatattca | tatccaagca | atggaagaga | 1200 |
| atggtcacaa | gaacaacctc | ccaagttatg | cttcacaaaa | gcccctgtga | aaacaacctt | 1260 |
| cctttcaat | ggtgtacatc | ctagtgtata | aatttgatgt | taggtgtgtt | attattctct | 1320 |
| tgctgtgaat | ccaggtaaaa | gtcattgtaa | tttggtcagt | cctcctctgc | tggaaaagcc | 1380 |
| ttgtgctttc | aatgcttggt | agaatataga | atcaagtgaa | tagtgtatct | tttcgatcaa | 1440 |
| tgttttgtgc | ttgtaagttg | aaaaaaaatg | tacaatgagg | tttatattg | tatccattta | 1500 |
| tgggattgta | cttactattc | acaacttagt | tgatttgact | cgactttcaa | atcacttgta | 1560 |
| tcgtattcac | gcggtttagt | gattaatgaa | atgaaaatag | gttgataacg | ataaatgtta | 1620 |
| gtattcacgc | ggtttagtga | ttaatgaaat | gaaataggt | tgataacgat | aaatgttagt | 1680 |
| gacgaataat | tctaaaattg | ctggcataca | gtatcaccca | aacaaatgga | tatttacgac | 1740 |
| aaatcaattt | tnnacttgat | acaagtaaat | ttttatcatt | actttaaaag | tgtatatata | 1800 |

FIGURE 3

```
tatatatgat taggtaaaca ttattttgcc gacccaaacc aagaaaaaac aataaaatta   1860
gctacaagta gtgtatcatt tgcccacttt cctccactag ttatccaaaa tgcccaccaa   1920
agagcacaac tccttaaga tacctttttc ccttgccta ataaacttgt tttggtcaca    1980
gtttgtaaaa aaaaaatta aatgtttttg aataataaca taaaaaatta ttttttgaa    2040
aagatgaaaa aaataaattc ctttaaaaa tacttgcaac aataagatt tctcaaaata    2100
atttttta tgtcgtgtaa tttgattttc cacctcggaa tcctcttttc tagttactct    2160
acccccaatt tttatttatt tgttgaaaaa aactaagaac ttggccaaga caggtttata   2220
tatttaccaa aactacacac ttagagctca cataatcttg taaaaatggc aacttcaatt   2280
tttctctcac acccttttc tcatttatta tcaaaacacc ataaaattcc aagtcctaaa   2340
caaaccatag ccatagcata tcactccacc aacaaaccca ccaccaagac tccattttta   2400
ccattaccca cttccttttt tccatttccc tcaaacccca gaaaggaatt ttgccaatt    2460
tcagtgggaa gaacacaaac agatgaaaaa gatgaaatct tgtggtggg tgaagattct    2520
gctgaatttg agttatccaa acaaaagatt tcatccttggg tttattttgc tggggttctt  2580
ggtgttgtgc tttatgttct taatgttgtt tggattgaca attctactgg atttggaaaa   2640
tcattcattg attctgtttc tagtattca gatagccctg aagtgagtat ttttgcttaa    2700
ttactttttc tgttctgttt ttatttactt ttgctgaatt gagtttttgag gtattgcttt  2760
tgattatgtt ctttacttgg taataatagt tgtataaatt gttagaacag taaaaaaatg   2820
atatcttttg tgaaaggtat aacgcataaa tatgtccttt aacttggcat atctgtgcct   2880
caaactttgg gcgtgcacac gttgatgctt aaacttgtat agagttaaaa catatgcatt   2940
ctatgtgtat gttaataata gaagagaatt attactcact ttggtgttcc attattctat   3000
tttatgtttc ttaactttat tgtatagtga ttataaaatt tttgtagttt tctggaacgg   3060
gacggagttc ccacttcttc ctagcacatt tgctctcctt gtagcacttc tgacaaagat   3120
ttagttattt ttcatatgca tattttctta ttgtagtgtt ccagcacacc tttactattt   3180
taccggtttt acttattttc tcttaccgat ataggtttta gtaactcta tccactaagc   3240
gttaggcaaa taggaagaga ttattaaacg cttctttgtt tttggccgct gtcggattt    3300
aaaccctggt cttcattcta gtctaagtga acgctaactc acacccttgt gcgacatcac   3360
```

FIGURE 3 (CONT 1)

```
ccactgattg ttgtcttatg aatttgttta caatgaaata tggcttaaga cttttaagtt   3420
ctgctatcta ggcttagca tataattgag ccgaggttct attgggaaca acctccctat    3480
cctgcaaagg ttggggtaag gtgtgcatac atcgtaccct ctccagaatc cagaccctat   3540
gttgttgttg tagattagca tataaattaa aggtgcaac atcagtcatc ccggcctct    3600
gtatattaaa aatcagggac tagtttaatc aatcagcact tgggattga gcttgtagga   3660
tcaagctttt aagcgttacg gagatgagaa aaagatagat aaaatctttt atctgcaaac   3720
tcccattcac aataattttg ttaattattt ttattgattt caatgtttgtt attttcttct  3780
ttgtttgttt gtcacttggt gttagtcttg tgtagttact ttggttaatt caaacgaaat   3840
tatggaattg gtttacgttc aagactttta caagggaag cttttgttag catagtttta   3900
tcaaagaact ctatgagata ccaactaata gtcaaacaag aaccaacgaa ggagggtcga   3960
tttgaagttg ttaaccaaca aggttactta tgtttggca actgtagaat aacattatgt    4020
cttcgccttg caatgaagac tatatagcct tgataatgct cggaaagtat ttatttgttc   4080
tggttcattc tgtcactctt cttgcttga taataggcaa gagatgcatt agattctcga    4140
tgaatatgca agagatgcat tagattctcg atgaatcata ttggccaaca taaaattgtc   4200
ttgatttctt tcctgttgtt tctttctttg tacacttagt tatttcacgt ccacttttgc   4260
catcttggta accagcatac actatataaa tttttcattt cgcgtaccaa aatttctgct   4320
ttctgagagt ttatccaaat gtttctatgc agattgtaat gctttccctt acctgattt    4380
tcgctatagt ccacagtggt cttgctagtc ttagagacaa aggtgaggaa ctcattggag   4440
agcgtgcttt tcgtgtattg tttgctgggg tatctctgcc attgcgcagtc agcacaattg  4500
tgagttttct agtctgccat gcagaaacta agaattttgt ttatttttt gggtaacttt    4560
tctgattta cggtgcgatg cttgatagat ggaaatttaa cataacggaa ggttcttatg    4620
atgattaca ggtgtatttc attaaccacc gatacgatgg agtgcagtta tggcaattaa    4680
acagtgttgc tgggattcac gaactagttt ggattctaa cttttgtttcc ttcttcttcc   4740
tataccgtc gacattcaat ttactagagg tagcggctgt tgacaagccc aagatgcatc    4800
tttgggaaac tgggattatg aggattacca gcatccaca gtaaatgct caattatcac     4860
ttaaatgtaa cctaccgttg tagaagatac agtctgaatg atttatata gtgccttgtc    4920
ccgaaacacc aatgcgtacc tttactttca aatctcttc caattaaat ttcaacgttt     4980
```

FIGURE 3 (CONT 2)

```
gattcaaatc acttcgcttt gtacctcgta ttacatttta attccaggat atgacacttg   5040
ggagggtagg atgtacgtac gctgacctta ctcctaccct tgtgggtag agaggttgtc   5100
tccgatagac tctcaggtca aagaagtgt aatcaaagca gataagatag gaagaaaaat   5160
aatgacaaca aaatactgag atatacagag caaatgaggc aacaggtgtt agaaaaagtt   5220
gaagaataag tactattaaa ggagaagatg agaagaggag actagccccc ttcctttccc   5280
acataaaaga acgacgacac tcgggtatct catacccttc taccctaaac tgaccatata   5340
ccctcctacc taggattatg tcttcagcaa gctgaagatt agaccccgg ttcttctatt   5400
ttccaggata tgacgcaagt actatgacag aggaggttta gagtcatgat ttctaatcat   5460
tatttctgta gggttcagga attctctctt tttagttttt tcgtgtattt cagtcagata   5520
ctcaaaatta taaatcactt ttgattctta gaaccaagaa gtggatttat cggtcaatgg   5580
ttttctctga aggagttgaa taaggcatgt cacaaagaat gatatctcaa gaaatgacgg   5640
gcagaggttg atgcagaacg agtctgtaca tgaaatgagg tgaaggttat tgtaatccca   5700
gttctgctaa taatacataa aagggaagaa acctaccaaa ttgataaagc tgttccataa   5760
ttgaggattt tagtaaagag aaatcatctc aagtcctgaa atcgagaaa ataagtgtct   5820
ttgtgcatat atgttacacg acagtccagt attcttgctt ctatttgctg tctcatttct   5880
tagtataagt tattccgtct ttgatagcta attgaagcct ccattcccta tattag_ctgg_   5940
t_cgggcaggt tatatggtgc ttagctcaca cgctgtggat tgggaattca gttgcagtgg_   6000
c_agcttcagt agtttgata ggacatcatc tgttggtgc ctggaatggg gaccggaggt_   6060
t_agccatacg atatggtgag gcttttgaag tcgtgaagaa cagaacgagt atcattccat_   6120
t_tgcagccat tcttgatggt cgtcaaaagt tgcctgaaga ttattacaag gaatttatca_   6180
g_attgccata tttatcgata acaacattga cattaggtgc ttacttcctc cacccatta_   6240
t_gcaagctgc cagttatcgg ctacactggt agtagtactg atgttacata actcgtttcc_   6300
a_tacaagata tcgcgattac gagttgtata ttttcctca atatatatag gttactgatg_   6360
t_ctatttaac tactgttgga taacaaagaa agaaagaaga ggaatagaga gaattcagtt_   6420
t_aatgtgttt gaaaagtaaag ttccaacttg tattccctt caatttctat atagtgtata_   6480
t_catgacata tatgtccttg ttattccaat atatatat atatggtacc aaagttttcg_   6540
a_gtttgagtt atgttaatga attattattt tttataaaac gcgatttatc tctttagatg_   6600
```

FIGURE 3 (CONT 3)

```
aacctcatgg tgtaaatttt gtttatttca tttagcggct tcaagtacca aataattaac    6660
taacggcatt atgtctgaat aaatgattca tcaaataaac gagttatcat taacattgag    6720
acatttgaaa tcgccaaata cgtaaaagtt tctcaaattt gattcatcta atgaacttca    6780
aatatcaagt aattaaaaa atgatgcaaa tatcaataat tttatggtca gacaaggcct    6840
acctaaaagg agcaagtcag cttggaccaa atccaaaaat gaaaaaaaaa acagattttt    6900
tttttttttt ttataaatta aacactattc cacttctggt gttgaggaat tatcaaataa    6960
aagtacacca aattcttttg acttttttt actttttgtg ataatgaaga aatacatgtg    7020
gccaatttga atgatatttt atattttaaat tcccttttga tttactcttc ctcatgcaat    7080
gtgattggaa gagtagggaa tgagtaggtt cacttaagaa tgctacactt aaccaatct    7140
gaataaattt ttcactcgat atttaatact aatcttaaag tcttattaaa tttaaattcg    7200
tatcgaaaaa tttcacatta aataataaga cattcccaa taagataact tcatgtccac    7260
gattcgaact caaatccta attattatcc acatacatat acttctagga acttttaa    7320
cgtggcatac atacatcact tatttcatca cacttaaaaa gaacatacaa gttatatgtc actataaata    7380
aattattaca taacgataac tatttcatca ttcttaatca gaaaaaatta tattcacgct    7440
tttggtataa aatcggtttt gataagtaac gcttacccc tacaaagtga aactgtatat    7500
tgatcgaagt ccaaaataaa tatcgaaaaa taatacaacc gtgtataaaa ctatgtaaac    7560
cccacccct ccacatacac acaaacactt catgggggtg gaggatttgg ttagtgtgct    7620
tttgttttta tttcataaaa attggactaa cattgggttg agttgcacag tttaaccaac    7680
tatattatat ccacttatt aagttctaa cccactccat cattttaat atttctaatt    7740
taatgccaca ttgccaccaa cctactttaa tattggtat gtcttacatt ttctataact    7800
aaaatcatac taacttctta ttaagccaa ttgcttaaca catctcatta ttattattat    7860
aactctcctt tctatttata taaatctttg tgatttatat gctattataa ttcactattg    7920
atttcatatt tcatatgcta attggaagaa atatgaagga aaaatcagta gagaaatttt    7980
tcatgttgcc attctatta gggtgtaatt ctgagtcaag tgttggagtg acaaaccaac    8040
ttgtggaaac aagaattca tcacaaataa c (SEQ ID NO:1)                      8071
```

FIGURE 3 (CONT 4)

```
   1 TGAATAATAA CATAAAAAAT TATTTTTTG AAAAGATGAA AAAAATAATT TCCTTTTAAA
  61 AATACTTGCA ACAAATAAAA TTTCTCAAAA TAATTTTTTT TATGTCGGGT AATTTGATTT
 121 TCCACCTCGG AATCCTCTTT TCTAGTTACT CTACCCCCAA TTTTTATTTA TTTGTTGAAA
 181 AAAACTAAAA ACTTGGCCAA GACAGGTTTA TATATTTACC AAAACTACAC ACTTAGAGCT
 241 CACATAACCT TGTAAAAATG GCAACTTCAA TTTTTCTCTC ACACCCTTTT TCTCATTTAT
 301 TATCAAAACA CCATAAAATT CCAAGTCCTA AACAAACCAT AGCCATAGCA TATCACTCCA
 361 CCAACAAACC CACCACCAAG ACTCCATTTT TACCATTACC CACTTCCTTT TTTCCATTTC
 421 CCTCAAACCC CAGAAAGGAA TTTTGGCCAA TTTCAGTGGG AAGAACACAA ACAGATGAAA
 481 AAGATGAAAT CTTGGTGGTG GGTGAAGATT CTGCTGAATT TGAGTTATCC AAACAAAAGA
 541 TTTCATCTTG GGTTTATTTT GCTGGGGTTC TTGGTGTTGT GCTTTATGTT CTTAATGTTG
 601 TTTGGATTGA CAATTCTACT GGATTTGGAA AATCATTCAT TGATTCTGTT TCTAGTATTT
 661 CAGATAGCCC TGAAATTGTA ATGCTTTCCC TTACCCTTGAT AACTCATTGG AGAGCGTGCT GTCCACAGTG
 721 GTCTTGCTAG TCTTAGAGAC AAAGGTGAGG AACTCATTGG AGAGCGTGCT TTTCGTGTAT
 781 TGTTTGCTGG GGTATCTCTG CCATTGGCAG TCAGCACAAT TGTGTATTTC ATTAACCACC
 841 GATACGATGG AGTGCAGTTA TGGCAATTAA ACAGTGTTGC TGGGATTCAC GAACTAGTTT
 901 GGATTTCTAA CTTTGTTTCC TCTTCTTCC TATACCCGTC GACATTCAAT TTACTAGAGG
 961 TAGCGGCTGT TGACAAGCCC AAGATGCATC TTTGGGAAAC TGGGATTATG AGGATTACCA
1021 GGCATCCACA GCTGGTCGGG CAGTTATAT GGTGCTTAGC TCACACGCTG TGGATTGGGA
1081 ATTCAGTTGC AGTGGCAGCT TCAGTAGGTT TGATAGGACA TCATCTGTTT GGTGCCTGA
1141 ATGGGGACCG GAGGTTAGCC ATACGATATG GTGAAGGCTTT TGAAGTCGTG AAGAACAGAA
1201 CGAGTATCAT TCCATTTGCA GCCATTCTTG ATGGTCGTCA AAAGTTGCCT GAAGATTATT
1261 ACAAGGAATT TATCAGATTG CCATATTTAT CGATAACAAC ATTGACATTA GGTGCTTACT
1321 TCCTCCACCC CATTATGCAA GCTGCCAGTT ATCGGCTACA CTGGTAGTAG TACTGATGTT
1381 ACATAACTCG TTTCCATACA AGATATCGCG ATTACGAGTT GTATATTTTT CCTCAATATA
1441 TATAGGTTAC TGATGTCTAT TTAACTACTG TTGGATAACA TTGGATAACAGAGT GAAGAGGAAT
1501 AGAGAGAATT CAGTTTAATG TGTTTGAAAG TAAAGTTCCA AAGAAAGAAA CCCTTCAATT
1561 TCTATATAGT GTATATCATG ACATATATGT CCTTGTTAT ACTTGTATTT (SEQ ID NO:2)
```

FIGURE 4

```
  1 TGAATAATAA CATAAAAAAT TATTTTTTTG AAAAGATGAA AAAAATAATT TCCTTTTAAA
 61 AATACTTGCA ACAAATAAAA TTTCTCAAAA TAATTTTTTT TATGTCGGGT AATTTGATTT
121 TCCACCTCGG AATCCTCTTT TCTAGTTACT CTACCCCCAA TTTTTATTTA TTTGTTGAAA
181 AAAACTAAAA ACTTGGCCAA GACAGGTTTA TATATTTACC AAAACTACAC ACTTAGAGCT
241 CACATAACCT TGTAAAAATG GCAACTTCAA TTTTTCTCTC ACACCCTTTT TCTCATTTAT
301 TATCAAAACA CCATAAAATT CCAAGTCCTA AACAAACCAT AGCCATAGCA TATCACTCCA
361 CCAACAAACC CACCACCAAG ACTCCATTTT TACCATTACC CACTTCCTTT TTTCCATTTC
421 CCTCAAACCC CAGAAAGGAA TTTTGGCCAA TTTCAGTGGG AAGAACACAA ACAGATGAAA
481 AAGATGAAAT CTTGGTGGTG GGTGAAGATT CTGCTGAATT TGAGTTATCC AAACAAAAGA
541 TTTCATCTTG GGTTTATTTT GCTGGGGTTC TTGGTGTTGT GCTTTATGTT CTTAATGTTG
601 TTTGGATTGA CAATTCTACT GGATTTGGAA AATCATTCAT TGATTCTGTT TCTAGTATTT
661 CAGATAGCCC TGAAATTGTA ATGCTTTCCC TTACCTTGAT TTTCGCTATA GTCCACAGTG
721 GTCTTGCTAG TCTTAGAGAC AAAGGTGAGG AACTCATTGG AGAGCCTGCT TTTCGTGTAT
781 TGTTTGCTGG GGTATCTCTG CCATTGGCAG TCAGCACAAT TGTGTATTTC ATTAACCACC
841 GATACGATGG AGTGCAGTTA TGGCAATTAA ACAGTGTGTC TGGGATTCAC GAACTAGTTT
901 GGATTTCTAA CTTTGTTTCC TTCTTCTTCC TATACCCGTC GACATTCAAT TTACTAGAGG
961 TAGCGGCTGT TGACAAGCCC AAGATGCATC TTTGGGAAAC TGGGATTATG AGGATTACCA
1021 GGCATCCACA GCTGGTCGGG CAGGTTATAT GGTGCTTAGC TCACACGCTG TGGATTGGGA
1081 ATTCAGTTGC AGTGGCAGCT TCAGTAGGTT TGATAGGACA TCATCTGTTT GGTGCCTAGA
1141 ATGGGACCG GAGGTTAGCC ATACGATATG GTGAGGCTTT TGAAGTCGTG AAGAACAGAA
1201 CGAGTATCAT TCCATTTGCA GCCATTCTTG ATGGTCGTCA AAAGTTGCCT GAAGATTATT
1261 ACAAGGAATT TATCAGATTG CCATATTTAT CGATAACAAC ATTGACATTA GGTGCTTACT
1321 TCCTCCACCC CATTATCCAA GCTGCCAGTT ATCGGCTACA CTGGTAGTAG TACTCATGTT
1381 ACATAACTCG TTTCCATACA AGATATCGCG ATTACGAGTT GTATATTTTT CCTCAATATA
1441 TATAGGTTAC TGATGTCTAT TTAACTACTG TTGGATAACA TTGGATAACA AAGAAAGAAA GAAGAGGAAT
1501 AGAGAGAATT CAGTTTAATG TGTTTGAAAG TAAAGTTCCA ACTTGTATTT CCCTTTCAATT
1561 TCTATATAGT GTATATCATG ACATATATGT CCTTGTTAT (SEQ ID NO:4)
```

```
   1  TGAATAATAA CATAAAAAAT TATTTTTTTG AAAAGATGAA AAAAATAATT TCCTTTTAAA
  61  AATACTTGCA ACAAATAAAA TTTCTCAAAA TAATTTTTTT TATGTCGGGT AATTTGATTT
 121  TCCACCTCGG AATCCTCTTT TCTAGTTACT CTACCCCCAA TTTTTATTTA TTTGTTGAAA
 181  AAAACTAAAA ACTTGGCCAA GACAGGTTTA TATATTTACC AAAACTACAC ACTTAGAGCT
 241  CACATAACCT TGTAAAAATG GCAACTTCAA TTTTTCTCTC ACACCCTTTT TCTCATTTAT
 301  TATCAAAACA CCATAAAATT CCAAGTCCTA AACAAACCAT AGCCATAGCA TATCACTCCA
 361  CCAACAAACC CACCACCAAG ACTCCATTTT TACCATTACC CACTTCCTTT TTTCCATTTC
 421  CCTCAAACCC CAGAAAGGAA TTTTGGCCAA TTTCAGTGGG AAGAACACAA ACAGATGAAA
 481  AAGATGAAAT CTTGGTGGTG GGTGAAGATT CTGCTGAATT TGAGTTATCC AAACAAAAGA
 541  TTTCATCTTG GGTTTATTTT GCTGGGGTTC TTGGTGTTGT GCTTTATGTT CTTAATGTTG
 601  TTTGGATTGA CAATTCTACT GGATTTGGAA AATCATTCAT TGATTCTGTT TCTAGTATTT
 661  CAGATAGCCC TGAAATTGTA ATGCTTTCCC TTACCTTGAT TTTCGCTATA GTCCACAGTG
 721  GTCTTGCTAG TCTTAGAGAC AAAGGTGAGG AACTCATTGG AGAGCGTGCT TTTCGTGTAT
 781  TGTTTGCTGG GGTATCTCTG CCATTGGCAG TCAGCACAAT TGTGTATTTC ATTAACCACC
 841  GATACGATGG AGTGCAGTTA TGGCAATTAA ACTGGTTGC TGGGATTCAC GAACTAGTTT
 901  GGATTTCTAA CTTTGTTTCC TTCTTCTTCC TATACCCGTC GACATTCAAT TTACTAGAGG
 961  TAGCGGCTGT TGACAAGCCC AAGATGCATC TTTAGGAAAC TGGGATTATG AGGATTACCA
1021  GGCATCCACA GCTGGTCGGG CAGGTTATAT GGTGCTTAGC TCACACGCTG TGGATTGGGA
1081  ATTCAGTTGC AGTGGCAGCT TCAGTAGGTT TGATAGGACA TCATCTGTTT GGTGCCTAGA
1141  ATGGGGACCG GAGGTTAGCC ATACGATATG GTGAGGCTTT TGAAGTCGTG AAGAACAGAA
1201  CGAGTATCAT TCCATTTGCA GCCATTCTTG ATGGTCGTCA AAAGTTGCCT GAAGATTATT
1261  ACAAGGAATT TATCAGATTG CCATATTTAT CGATAACAAC ATTGACATTA GGTGCTTACT
1321  TCCTCCACCC CATTATGCAA GCTGCCAGTT ATCGGCTACA CTGGTAGTAG TACTGATGTT
1381  ACATAACTCG TTTCCATACA AGATATCGCG ATTACGAGTT GTATATTTTT CCTCAATATA
1441  TATAGGTTAC TGATGTCTAT TTAACTACTG TTGGATAACA AAGAAAGAAA GAAGAGGAAT
1501  AGAGAGAATT CAGTTTAATG TGTTTGAAAG TAAAGTTCCA ACTTGTATTT CCCTTCAATT
1561  TCTATATAGT GTATATCATG ACATATATGT CCTTGTTAT (SEQ ID NO:6)
```

```
Ziso M82    1   MATSIFLSHPFSHLLSKHHKIPSPKQTIAIAYHSTNKPTTKTPFLPLPTSFFPFPSNPRKEFWPISVGRTQTDEK    75
ZISO 89         MATSIFLSHPFSHLLSKHHKIPSPKQTIAIAYHSTNKPTTKTPFLPLPTSFFPFPSNPRKEFWPISVGRTQTDEK
Ziso2083        MATSIFLSHPFSHLLSKHHKIPSPKQTIAIAYHSTNKPTTKTPFLPLPTSFFPFPSNPRKEFWPISVGRTQTDEK Ziso M82    76  DEILVVGEDSAEFELSKQKISSWVYFAGVLGVVLYVLNVVWIDNSTGFGKSFIDSVSSISDSPEIVMLSLTLIFA   150
ZISO 89         DEILVVGEDSAEFELSKQKISSWVYFAGVLGVVLYVLNVVWIDNSTGFGKSFIDSVSSISDSPEIVMLSLTLIFA
Ziso2083        DEILVVGEDSAEFELSKQKISSWVYFAGVLGVVLYVLNVVWIDNSTGFGKSFIDSVSSISDSPEIVMLSLTLIFA Ziso M82    151 IVHSGLASLRDKGEELIGERAFRVLFAGVSLPLAVSTIVYFINHRYDGVQLMQLNSVAGIHELVWISNFVSFFFL   225
ZISO 89         IVHSGLASLRDKGEELIGERAFRVLFAGVSLPLAVSTIVYFINHRYDGVQLMQLNSVAGIHELVWISNFVSFFFL
Ziso2083        IVHSGLASLRDKGEELIGERAFRVLFAGVSLPLAVSTIVYFINHRYDGVQLMQLNSVAGIHELVWISNFVSFFFL Ziso M82    226 YPSTFNLLEVAAVDKPKMHLWETGIMRITRHPQLVGQVIWCLAHTLWIGNSVAVAASVGLIGHHLFGAWNGDRRL   300
ZISO 89         YPSTFNLLEVAAVDKPKMHLWETGIMRITRHPQLVGQVIWCLAHTLWIGNSVAVAASVGLIGHHLFGA* (SEQ ID NO:5)
Ziso2083        YPSTFNLLEVAAVDKPKMHLWETGIMRITRHPQLVGQVIWCLAHTLWIGNSVAVAASVGLIGHHLFGA*
                                                                          (SEQ ID NO:7)

Ziso M82    301 AIRYGEAFEVVKNRTSIIPFAAILDGRQKLPEDYYKEFIRLPYLSITTLTLGAYFLHPIMQAASYRLHW   369
                                                                          (SEQ ID NO:3)
```

FIGURE 5C

```
Ziso 7942    (1)   ------------------------------------------------------------
Ziso M82 f   (1)   MATSIFLSHPFSHLLSKHHKIPSPKQTIAIAYHSTNKPTTKTPFLPLPTSFFPSNPRK Ziso 7942    (1)   ------------------------------------------------------------
Ziso M82 f  (61)   EFWPISVGRTQTDEKDEILVVGEDSAEFELSKQKISSWVYFAGVLGVLYVLNVVWIDNS Ziso 7942    (1)   -----MPLSWWTPSHTMLLLLFAIAHSGLALRPWGETKIGARRLFALVS
Ziso M82 f (121)   TGFGKSFIDSVSSISDSPEIMILTLFAIVHSGLALRDKGEIGERRLFAGVS Ziso 7942   (52)   LPLAVVTISYFILHRYDGALLWQLIGPWIAPLVWLTASFLLYPTFNLLEAAAQ
Ziso M82 f (181)   LPLAVSTIVYFINHRYDGVQLWQLSAGIHELVWSNFSFFLYPTFNLLEAADK Ziso 7942  (112)   PQQRLETGITRITRHPQTFGQXWCLAHLWGTSFMIVASAGLIHHLFSIWHGDRRL
Ziso M82 f (241)   PKMHLETGIMRITRHPQLVGQXWCLAHLWGNSVAAASVGLIHHLFGAWNGDRRL Ziso 7942  (172)   QKRYGEAFEAKSRTSIIPFIAIAQGTLVWKEILRPAYLGVAIAIGLFWFARWIPQA
Ziso M82 f (301)   AIRYGEAFEVKNRTSIIPFAAILDGQKLPEDYKEFIRLPYLSITTLTLGAFLHPIM Ziso 7942  (232)   TAALAEGW(SEQ ID NO:8)
Ziso M82 f (361)   QAASYRHW(SEQ ID NO:3)
```

FIGURE 7

ORGANISM WITH ALTERED CAROTENOID CONTENT AND METHOD OF PRODUCING SAME

RELATED APPLICATION DATA

This application is the U.S. National Stage of International Application No. PCT/IL2011/000225, filed Mar. 9, 2011, which claims the benefit of U.S. Provisional Application No. 61/312,082, filed Mar. 9, 2010, the contents of each of which are herein expressly incorporated by reference for all purposes.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 28,124 byte ASCII (text) file named "Seq_List" created on Sep. 5, 2012.

FIELD OF THE INVENTION

The present invention relates to genetically altered organisms producing elevated content of the carotenoids phytoene, phytofluene, zeta carotene or combinations thereof and to means and methods for producing same.

BACKGROUND OF THE INVENTION

Carotenoids are 40-carbon isoprenoid pigments synthesized by all plants, algae and cyanobacteria as well as by several non-photosynthetic bacteria and fungi. In plants, carotenoids are synthesized within plastids. The central pathway of isoprenoid biosynthesis in plastids begins with the production of isopentyl diphosphate (IPP), a $C_5$ molecule which is the building block for all long-chain isoprenoids, from pyruvate and glyceraldehyde 3-phosphate in the 2-C-methyl-d-erythritol 4-phosphate (MEP) pathway. Following isomerization of IPP to dimethylallyl pyrophosphate (DMAPP), three additional molecules of IPP are combined to yield the $C_{20}$ molecule, geranylgeranyl pyrophosphate (GGPP). These 1'-4 condensation reactions are catalyzed by prenyl transferase-type enzymes GGPP synthases. There is evidence in plants that the same enzyme, GGPP synthase, carries out all the reactions from DMAPP to GGPP.

The polyene chain of carotenoids may extend from 3 to 15 conjugated double bonds, which are responsible for the carotenoid characteristic absorption spectra and confer specific photochemical properties. Due to these properties carotenoids are essential components in all photosynthetic organisms, where they fulfill indispensable functions in photosynthesis. Carotenoids also play a part in plant reproduction by furnishing flowers and fruits with distinct pigmentation designed to attract animals and enhance pollination and seed dispersion. Many of the orange, yellow, or red colors found in these organs are generated by accumulation of high concentration of carotenoids in the chromoplasts. In addition, degradation products of carotenoids comprise aromatic and flavoring compounds, and their presence in fruit appeal to animals.

In the last decade, carotenoid biosynthesis in plants has been described at the molecular level (reviewed in, e.g. Lu, S. and Li, L. 2008. J. Integr. Plant Biol. 50:778-785). The first committed step in the carotenoid pathway is the head to head condensation of two GGDP molecules to produce phytoene, the first C40 carotenoid, catalyzed by the enzyme phytoene synthase (PSY).

Insertion of conjugated double bonds (carotene desaturation) into the C40 chain of phytoene leads to the formation of visible polyene chromophore. The plant carotene desaturation is a membrane-bound complex reaction sequence. Four double bonds are introduced to phytoene by two enzymes, phytoene desaturase (PDS) and ζ-carotene desaturase (ZDS), each catalyzing two symmetric desaturation steps to yield ζ-carotene and lycopene, respectively (FIG. 1). It was recently established that all intermediates in this part of the pathway are cis-configured and that a specific isomerase, CRTISO, operates in conjunction with ZDS to produce all-trans lycopene (Isaacson, T. et al. 2002. Plant Cell 14:333-342; Isaacson, T. et al. 2004. Plant Physiol. 136:4246-4255; Park, H. et al. 2002. Plant Cell 14:321-332). In addition, it has been predicted that other enzymes and cofactors are essential for this process, including a factor designated Z-ISO which is involved in 15-cis-ζ-carotene isomerization (Li F. et al. 2007. Plant Physiol. 144:1181-1189). Carotene desaturation is a redox reaction, linked to an extended redox chain, employing quinones as intermediate and molecular oxygen as a terminal electron acceptor. Molecular oxygen is reduced by means of a plastidic "terminal" ("alternative") oxidase. Due to this complexity and the membrane-bound topology of the enzymes involved, a PDS-ZDS desaturation system has never been reconstructed in vitro with purified proteins. A paper of Chen Y. et al., published after the priority of the present invention describes the isolation and characterization of Z-ISO gene, and proposed that the encoded protein has a role in isomerization of the 15-cis-bond present in the PDS product, 9,15,9'-tri-cis-ζ-carotene to form the ZDS substrate 9,9'di-cis-ζ-carotene.

Cyclization of lycopene by either lycopene β-cyclase (Lcy-b) or lycopene epsilon-cyclase (Lcy-e), lead to β-carotene and α-carotene, respectively. Oxygenations of cyclic carotenes produce xanthophylls. In bacteria, a single phytoene desaturase enzyme, CrtI, carries out the phytoene to trans-lycopene conversion. Surprisingly, a transgenic CrtI desaturase is active in plants.

In plants, carotenoids are also precursors for growth regulators and developmental signals. The hormone abscisic acid (ABA) is produced from the xanthophylls violaxanthin and neoxanthin. It has been recently discovered that a cleavage derivative of β-carotene, possibly 13-apo-β-carotenone, serves as a graft-transmissible inhibitor of lateral shoot branching in Arabidopsis.

There is growing interest worldwide in increasing the content of vitamins and other functional nutrients in crop plants (DellaPenna, D. 1999. Science 285:375-379; Lindsay, D. G. 2000. Trends in Food Sci. Technol. 11:145-151). Carotenoids play crucial role in determining quality parameters of fruits and vegetables (reviewed in van den Berg, H. et al. 2000. J. Sci. Food Agric. 80:880-912). All carotenoid species that contain β-ring can be converted to retinol and thus are precursors of vitamin A (pro-vitamin A). While this is the major importance of carotenoids in human nutrition, additional health benefits are attributed to their antioxidant activity in vivo (Stahl, W. and Sies, H. 2003. Mol. Aspects Med. 24:345-351). Consumption of xanthophylls (especially lutein) has been associated with prevention of age-related macular degeneration.

Epidemiological studies have associated carotenoids with reduces risk of cancer and other diseases in humans (Cooper, D. A. 2004. J Nutr. 134:221S-224S). Specific health benefits have been attributed to the carotenoids phytoene and phytofluene (Shaish, A. et al. 2008. Plant Foods Hum. Nutr. 63:83-86). Significant uptake of phytoene and phytofluene from tomato-based products was reported in humans (Aust, O. et al. 2005), and it was found that they are readily absorbed by normal and prostate tumor cells (Campbell, J. K. et al. 2007. Nutr. Res. 27:794-801). Phytoene was demonstrated in animal models as an effective sunscreen (Mathews-Roth, M. M. and Pathak, M. A. 1975. Photochem. Photobiol. 21:261-263).

Phytoene and phytofluene absorb light in the ultraviolet wavelength range. The absorption spectrum of phytoene is 276-297 nm (major peak 285-287 nm) and of phytofluene 331-367 (major peak 348 nm). Zeta-carotene absorption spectrum is 374-425 nm (major peak 395-400 nm). Therefore, these carotenoids may be used as sunscreen to protect the skin from damages inflicted by ultraviolet (UV) light. Indeed, protection of skin from UV light was demonstrated in humans fed with tomato-based foods or extracts (Stahl, W. et al. 2001. J. Nutr. 131:1449-1451), and this effect was attributed to phytoene and phytofluene (Aust, O. et al. 2005. Int. J. Vitam. Nutr. Res. 75:54-60). Based on these studies, it has been suggested that dietary carotenoids may contribute to life-long protection against harmful UV radiation (Stahl, W. et al. 2006. Photochem. Photobiol. Sci. 5:238-242). The potential of using phytoene and phytofluene as sunscreen is supported by previous studies that showed benefit in combining topical treatment with carotenoids in addition to oral supplementation (Palombo, P. et al. 2007. Skin Pharmacol. Physiol. 20:199-210). Accumulation of phytoene and to some extent of phytofluene has been reported upon the addition of the herbicide norflurazon (4-chloro-5(methylamino)-2-(3-(trifluoromethyl)phenyl)-3(2H)-pyridazinone) to the growth medium of the algae Dunaliella (Ben Amotz, A. et al. 1987 J. Phycol., 23:176-181). However, the use of such chemicals is possible only in culture-grown organisms.

The amount of phytoene and phytofluene, being the first ingredients in the carotenoid pathway, is relatively low in carotenoid-containing organisms. In view of the beneficial effects reported for phytoene and phytofluene, there is a recognized need for, and would be highly advantageous to have, carotenoid producing organisms having high amounts of phytoene and phytofluene.

SUMMARY OF THE INVENTION

The present invention relates to biotechnologically means and methods for modifying the expression of a component in the carotenoid biosynthetic pathway as to attenuate the production of carotenoids towards accumulation of at least one of phytoene, phytofluene, zeta carotene or combinations thereof. The present invention further relates to genetically altered organisms having elevated content of these carotenoids and to methods of producing same.

The present invention is based in part on the unexpected discovery that tomato plants comprising ZETA mutations produce fruit with elevated amounts of the carotenoids phytoene, phytofluene and zeta-carotene compared to the corresponding wild type tomato. Elevated content of these carotenoids was also measured in flowers, roots and etiolated leaves of the ZETA tomato plants. The ZETA mutations and the encoded proteins are characterized in the present invention for the first time, as well as the sequence of the wild type tomato gene and protein.

Without wishing to be bound by any particular theory or mechanism of action, a protein, designated Ziso, is required for proper isomerization of zeta-carotene. As demonstrated in tomato plants, its absence or lack of activity in ZETA mutants, particularly in chromoplast-containing cells, arrests the carotenoid biosynthetic pathway after the production of zeta carotene, leading to accumulation of the previous components, mainly phytoene and phytofluene.

The present invention thus provides means and methods for inhibiting the Ziso protein expression and/or function. As a result, the carotenoid biosynthetic pathway distal to zeta-carotene isomerization is blocked or attenuated, thereby leading to accumulation of phytoene and phytofluene. In some embodiments the phytoene and phytofluene accumulate to hitherto unheard off amounts of at least 15% phytofluene and 25% phytoene out of the total carotenoid content. The present invention further provides genetically altered organisms, particularly higher plants, with reduced Ziso expression or activity and elevated content of at least one of phytoene, phytofluene and optionally further zeta carotene compared to non-altered organisms.

According to one aspect, the present invention provides a genetically altered carotenoid-producing organism comprising at least one cell having reduced expression or activity of Ziso compared to a corresponding non-altered organism, wherein the genetically altered organism has an elevated content of at least one carotenoid selected from the group consisting of phytoene, phytofluene, zeta carotene and combinations thereof compared to a corresponding non-altered organism.

According to certain embodiments, the genetically altered organism comprises elevated content of phytoene compared to a corresponding non-altered organism. According to additional embodiments, the genetically altered organism comprises elevated content of phytofluene compared to a corresponding non-altered organism. According to yet further embodiments, the genetically altered organism comprises elevated content of a combination of phytoene and phytofluene compared to a corresponding non-altered organism.

According to certain embodiments, the cell having reduced expression or activity of Ziso is a chromoplast-containing cell. According to other embodiments, the cell having reduced expression or activity of Ziso is of non-photosynthetic tissue. Each possibility represents a separate embodiment of the present invention.

According to certain embodiments, the carotenoid-producing organism is selected from the group consisting of a plant, an alga and a cyanobacterium. According to certain typical embodiments, the carotenoid-producing organism is a plant. According to yet other typical embodiments, the plant is a tomato plant. When the organism is a plant, the elevated content of phytoene, phytoene, zeta-carotene or combinations thereof is present in at least one organ of the plant. According to typical embodiments, the organ is selected from the group consisting of fruit and roots. According to additional typical embodiments, the elevated content of at least one of phytoene, phytofluene and zeta-carotene is present in fleshy fruit tissues. Each possibility represents a separate embodiment of the present invention.

Inhibiting the expression or activity of the Ziso protein may be achieved by various means, all of which are explicitly encompassed within the scope of present invention. According to certain embodiments, inhibiting Ziso expression can be affected at the genomic and/or the transcript level using a variety of molecules that interfere with transcription and/or translation (e.g., antisense, siRNA, Ribozyme, or DNAzyme) of the Ziso gene. Inserting a mutation to the Ziso gene, including deletions, insertions, site specific mutations, mutations mediated by zinc-finger nucleases and the like can be also used, as long as the mutation results in down-regulation of the gene expression or in non-function protein. Alternatively, expression can be inhibited at the protein level using, e.g., antagonists, enzymes that cleave the polypeptide, and the like.

According to certain embodiments, the wild type unmodified Ziso protein of the organism comprises an amino acid sequence at least 55%, typically at least 60%, 70%, 75%, more typically at least 80%, 85%, 95% and more homologous to the amino acid sequence set forth in SEQ ID NO:3. According to typical embodiments, the unmodified Ziso protein comprises the amino acid sequence set forth in SEQ ID NO:3. Each possibility represents a separate embodiment of the present invention.

According to additional embodiments, the wild type unmodified Ziso gene comprises a nucleic acid sequence at least 55%, typically at least 60%, 70%, 75%, more typically at least 80%, 85%, 95% or more homologous to the nucleic acid sequence set forth any one of SEQ ID NO:1 and SEQ ID NO:2. According to typical embodiments, the unmodified Ziso gene comprises the nucleic acids sequence set forth in any one of SEQ ID NO:1 and SEQ ID NO:2. Each possibility represents a separate embodiment of the present invention.

According to certain embodiments, the genetically altered organism comprises a mutated Ziso gene. Mutations can be enforced on a plurality of organisms by any method as is known in the art, including applying mutagenic chemicals or radiation. The plurality of organisms is then screened for the specific phenotype of arrest in carotenoid biosynthesis at the stage of zeta-carotene, specifically the accumulation of 9,15,9'-tri-cis-zeta-carotene. The plurality of organisms can be also screened for specific mutations in the Ziso gene by methods of molecular tilling (McCallum, C. M. et al. 2000. Nat Biotechnol. 18:455-457). Organisms having the desired phenotype are then further screened for having elevated content of phytoene and/or phytofluene compared to a corresponding non-altered organism According to some embodiments, the mutated gene encodes a non-functional Ziso protein. According to certain typical embodiments, the mutated gene comprises the nucleic acids sequence set forth in SEQ ID NO:4 (designated ZETA$^{0089}$), encoding a non-functional Ziso protein having SEQ ID NO:5. According to additional typical embodiments the mutated gene comprises the nucleic acid sequence set forth in SEQ ID NO:6 (designated ZETA$^{2803}$) encoding a non-functional Ziso protein having SEQ ID NO:7.

According to additional embodiments, the genetically altered organism is a transgenic organism comprising at least one cell comprising a Ziso silencing molecule selected from the group consisting of RNA interference molecule, an antisense molecule and a ribozyme-encoding molecule.

The Ziso silencing molecule can be designed as is known to a person skilled in the art. According to certain embodiments, the silencing molecule comprises a polynucleotide having a nucleic acid sequence substantially complementary to a region of the expressed Ziso gene. According to certain embodiments, the Ziso gene comprises a nucleic acid sequence at least 55%, typically at least 60%, 70%, 75%, more typically at least 80%, 85%, 95% and more homologous to the nucleic acid sequence set forth in SEQ ID NO:2. According to other embodiments, the Ziso gene comprises the nucleic acid sequence set forth in SEQ ID NO:2. Each possibility represents a separate embodiment of the present invention.

According to certain embodiments, the complementary region is of a length of 20-500 nucleotides. According to some embodiments, the complementary region is of a length of 20-50 nucleotides, typically 20-30 nucleotides. According to other embodiments, the complementary region is of a length of 100-400 nucleotides, typically 200-300 nucleotides.

According to certain embodiments, the silencing molecule is an antisense RNA. According to other embodiments, the silencing molecule is an RNA interference (RNAi) molecule. According to additional embodiments, the RNAi molecule is designed to produce dsRNA targeted to a Ziso gene having a nucleic acid sequence at least 55%, typically at least 60%, 70%, 75%, more typically at least 80%, 85%, 95% and more homologous to the nucleic acid sequence set forth in SEQ ID NO:2. According to other embodiments, the Ziso gene has the nucleic acid sequence set forth in SEQ ID NO:2. Each possibility represents a separate embodiment of the present invention.

According to some embodiments, the silencing molecules of the present invention are incorporated in a DNA construct enabling their expression in cells of the organism. According to certain embodiments, the cell is a chromoplast-containing cell. According to other embodiments, the cell is within non-photosynthetic tissues. DNA constructs suitable to a particular organism, including plants, algae and cyanobacteria are known to a person skilled in the art. According to one embodiment, the DNA construct comprises at least one expression regulating element selected from the group consisting of a promoter, an enhancer, an origin of replication, a transcription termination sequence, a polyadenylation signal and the like. Typically, the promoter is a tissue specific promoter. According to certain embodiments, the tissue is a chromoplast-containing tissue. According to other embodiments, the tissue is non-photosynthetic tissue. When the organism is a plant, the promoter is typically specific to a tissue selected from the group consisting of roots, tubers, fruit, flowers and seeds. Each possibility represents a separate embodiment of the present invention.

According to certain embodiments, the genetically altered organism of the present invention has a phytoene content of at least 25% (w/w) of the total carotenoid content of the genetically altered cells. According to certain typical embodiments the phytoene content is at least 30%, more typically at least 35%, 40%, 45%, 50%, 55%, 60%, 65%, 70% or 75% of the total amount of carotenoids (w/w) of the genetically altered cells. Each possibility represents a separate embodiment of the present invention.

According to other embodiments, the genetically altered organism of the present invention has a phytofluene content of at least 15% (w/w) of the total carotenoid content of the genetically altered cells. According to certain typical embodiments the phytofluene content is at least 20%, more typically at least 25%, 30%, 35%, 40%, 45%, 50%, 55%, 60%, 65%, 70% or 75% of the total amount of carotenoids (w/w) of the genetically altered cells. Each possibility represents a separate embodiment of the present invention.

According to yet additional embodiments, the genetically altered organism of the present invention has a combined level of phytoene and phytofluene of at least 30% (w/w) of the total carotenoid content. According to certain typical embodiments, the combined level of phytoene and phytofluene is at least 35%, 40%, 45%, 50%, 55%, 60%, 65%, 70%, 75%, 80%, 85% 90% or 95% of the total amount of carotenoids (w/w) of the genetically altered cells. Each possibility represents a separate embodiment of the present invention.

It is to be explicitly understood that when the organism is a plant, the percentage of phytoene, phytofluene or their combination refers to their percentage in at least one of the plant organs. According to typical embodiments, the plant organ is selected from a root, a tuber, a fruit a flower and a seed.

Suspensions of genetically altered cells and tissue cultures derived from the genetically altered cells or organisms are also encompassed within the scope of the present invention. The cell suspension and tissue cultures may be used for the production of at least one of phytoene, phytofluene, zeta carotene or combinations thereof, which are then extracted from the cells or the growth medium. Alternatively, the genetically altered cells and/or tissue culture are used for regenerating an organism having reduced expression of the Ziso protein, therefore having elevated content of at least one of phytoene, phytofluene, zeta carotene or combinations thereof as disclosed herein.

In the embodiments wherein the organism is a plant, the present invention also encompasses seeds of the genetically altered plant, wherein plants grown from said seeds have reduced expression of Ziso compared to plants grown from corresponding non-altered seeds, thereby having an elevated content of at least one of phytoene, phytofluene, zeta carotene or combinations thereof as disclosed herein. Edible parts including fruit and tubers produced by the genetically altered plant of the invention, having phytoene and phytofluene content of at least 25% and 15% of the total carotenoid content, respectively, are also explicitly encompassed within the scope of the present invention.

According to a further aspect, the present invention provides a method of elevating the content of at least one of phytoene, phytofluene, zeta carotene or combinations thereof in at least one cell of an organism, comprising inhibiting the Ziso protein expression in the at least one cell, thereby producing an organism having an elevated amount of phytoene, phytofluene, zeta carotene or combinations thereof.

According to certain embodiments, inhibiting the Ziso expression comprises introducing a mutation in the Ziso encoding gene, wherein the mutation results in reduced expression of the Ziso gene or in the production of non-functional Ziso protein. Any method for introducing a mutation in the Ziso gene as disclosed herein and as is known in the art can be used according to the teachings of the present invention.

According to some embodiments, inhibiting the Ziso expression comprises transforming at least one cell of the organism with a molecule designed to silence the expression of the Ziso gene. According to certain embodiments, the Ziso gene comprises a nucleic acid sequence at least 55%, typically at least 60%, 70%, 75%, more typically at least 80%, 85%, 95% and more homologous to the nucleic acid sequence set forth in SEQ ID NO:2. According to other embodiments, the Ziso gene comprises the nucleic acid sequence set forth in SEQ ID NO:2. Each possibility represents a separate embodiment of the present invention. According to certain embodiments, the silencing molecule is selected from the group consisting of an antisense molecule, an RNAi molecule, a ribozyme encoding polynucleotide and the like.

According to certain embodiments, the organism produced by the method of the present invention has a phytoene content of at least 25% (w/w) of the total carotenoid, or a phytofluene content of at least 15% (w/w) of the total carotenoid content, or a combined level of phytoene and phytofluene of at least 30% (w/w) of the total carotenoid content.

According to other embodiments, the organism is a plant, having the elevated carotenoid content in at least one of his organs.

According to yet additional aspect, the present invention provides an isolated polynucleotide encoding non-functional Ziso protein having an amino acid sequence selected from the group consisting of SEQ ID NO:5 and SEQ ID NO:7. According to some embodiments, the isolated polynucleotide comprises a nucleic acid sequence set forth in SEQ ID NO: 4 and 6, respectively.

Other objects, features and advantages of the present invention will become clear from the following description and drawings.

BRIEF DESCRIPTION OF THE FIGURES

FIG. 3 shows the genomic sequence of the gene Ziso from tomato (predicted exons sequences are indicated in bold letters).

FIG. 4 shows the cDNA sequence of the gene Ziso from tomato (cv M82). The initiation codon (ATG) and termination codon are marked.

FIG. 5 shows the cDNA sequence of the gene Ziso from the tomato ZETA mutant allele $z^{0089}$, with the mutation creating a new stop codon indicated (FIG. 5A); the cDNA sequence of the gene Ziso from the tomato ZETA mutant allele $z^{2083}$, with the mutation creating a new stop codon indicated (FIG. 5B; and alignment of amino acid sequences of the polypeptide ZISO from the wild type tomato (CV M82) and ZETA mutants (alleles $z^{2083}$ and $z^{0089}$) as inferred from cDNA sequences (FIG. 5C).

FIG. 7 presents alignment of amino acid sequences of the polypeptide ZISO from the wild type tomato (CV M82) and ZETA-like gene-product of Synpcc7942_1979 (ZISO 7942) from *Synechococcus elongatus* PCC7942. Identities are marked in white fonts over black background; similarities as black fonts over gray background.

DETAILED DESCRIPTION OF THE INVENTION

Figure 1:
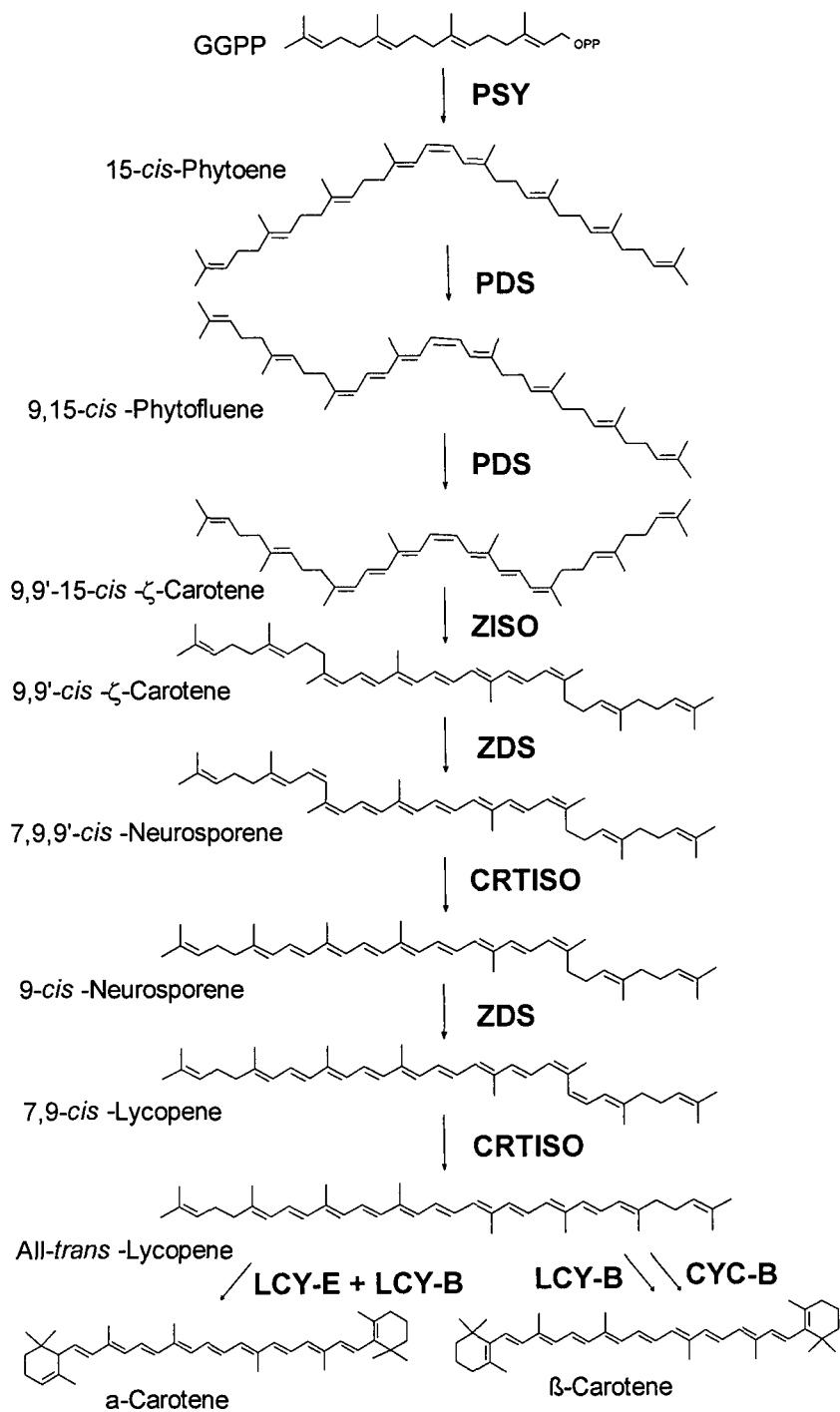
FIG. 1 shows schematic presentation of the carotenoid biosynthesis pathway in plants from geranylgeranyl diphosphate to β-carotene. CRTISO, carotene isomerase; CYC-B, chromoplasts-specific lycopene β-cyclase; GGPP, geranylgeranyl diphosphate; LCY-B, lycopene β-cyclase; LCY-E, lycopene ε-cyclase; PDS, phytoene desaturase; PSY, phytoene synthase; ZDS, ζ-carotene desaturase; ZISO, ζ-carotene isomerase.

The present invention relates to means and methods for producing at least one of phytoene, phytofluene, zeta carotene or combinations thereof in carotenoid-synthesizing organisms. Particularly, the present invention relates to organisms genetically altered by biotechnological means, in which the expression or activity of the Ziso protein is inhibited, such that the carotenoid biosynthesis pathway is arrested after the production of 9,15,9'-tri-cis-zeta-carotene, and phytoene and/or phytofluene are accumulated to levels of at least 25% and 15% (w/w) of the total carotenoid level, respectively, in the genetically altered cells. According to certain typical embodiments, the organism is a plant, typically tomato plant.

Definitions

The term "carotenoid producing organism" refers to an organism naturally capable of producing carotenoids, in which the carotenoid biosynthesis pathway comprises the step of zeta-carotene isomerization. According to certain embodiments of the present invention, the organism is selected from the group consisting of plants, algae and cyanobacteria.

The term "genetically altered organism" refers to an organism comprising at least one cell genetically altered by man. The genetic modification includes modification of an endogenous gene(s), for example by introducing mutation(s) deletions, insertions, transposable element(s) and the like into an endogenous polynucleotide or gene of interest. Additionally or alternatively, the genetic modification includes transforming the organism cell with heterologous polynucleotide to produce transgenic organism.

The term "phytoene" refers to 15Z-7,8,11,12,7',8',11',12'-octahydro-ψ,ψ-carotene.

The term "phytofluene" refers to 15Z-7,8,11,12,7',8'-hexahydro-ψ,ψ-carotene.

The term "zeta-carotene" refers to 7,8,7',8'-tetrahydro-ψ, ψ-carotene

The term "tri-cis-zeta-carotene" refers to 9Z,15Z,9'Z-7,8, 7',8'-tetrahydro-ψ,ψ-carotene.

The terms "Ziso" and "Ziso protein" are used herein interchangeably and refer to a protein the presence or activity of which is required for the isomerization of zeta-carotene. According to certain embodiments, the native, unmodified Ziso protein comprises the amino acid sequence set forth in SEQ ID NO:3 or a sequence homologous thereto. It is to be explicitly understood that orthologs of the tomato Ziso, having the same function, even if sharing low sequence homology with the tomato protein, are also encompassed within the teachings of the present invention.

As used herein the term "cis-carotenoid" refers to a carotenoid having at least one double-bond connecting two carbons in a cis orientation.

As use herein, the term "zeta carotene isomerization" refers to the conversion of 9,9'-15-cis-ζ carotene to 9,9'-cis-ζ carotene.

The term "gene" refers to a nucleic acid (e.g., DNA or RNA) sequence that comprises coding sequences necessary for the production of RNA or a polypeptide. A polypeptide can be encoded by a full-length coding sequence or by any part thereof. The term "parts thereof" when used in reference to a gene refers to fragments of that gene. The fragments may range in size from a few nucleotides to the entire gene sequence minus one nucleotide. Thus, "a nucleic acid sequence comprising at least a part of a gene" may comprise fragments of the gene or the entire gene.

The term "gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences.

The terms "Ziso" and "Ziso gene" are used herein interchangeably and refer to a polynucleotide encoding the Ziso protein. According to certain typical embodiments of the present invention the Ziso gene comprises the nucleic acid sequence set forth in SEQ ID NO:1, SEQ ID NO:2 or a sequence homolog thereto.

The terms "homolog" or "homologues" as referring to polypeptides or proteins are used herein to mean polypeptides with any insertions, deletions and substitutions which do not affect the biological activity of the polypeptide as described herein. Polypeptides homologous to the Ziso protein can be determined using the basic local alignment search tool BLAST®P or TBLAST®N software of the National Center of Biotechnology Information (NCBI) using default parameters, optionally and preferably including the following: filtering "on" (this option filters repetitive or low-complexity sequences from the query using the Seg (protein program), scoring matrix is BLOSUM62 for proteins, word size is 3, E value is 10 and gap costs are 11, 1 (initialization and extension).

When referring to polynucleotides the terms "homolog" or "homologous" mean polynucleotide encoding a polypeptide or protein having the biological activity of Ziso as described herein. According to certain embodiments, nucleic acid sequence homology/identity is determined by using BLAST®N software of the National Center of Biotechnology Information (NCBI) using default parameters, which preferably include using the DUST filter program, and also preferably include having an E value of 10, filtering low complexity sequences and a word size of 11.

The terms "polynucleotide", "polynucleotide sequence", "nucleic acid sequence", and "isolated polynucleotide" are used interchangeably herein. These terms encompass nucleotide sequences and the like. A polynucleotide may be a polymer of RNA or DNA or hybrid thereof, that is single- or double-stranded, linear or branched, and that optionally contains synthetic, non-natural or altered nucleotide bases. The terms also encompass RNA/DNA hybrids.

The terms "complementary" or "complement thereof" are used herein to refer to the sequences of polynucleotides which is capable of forming Watson & Crick base pairing with another specified polynucleotide throughout the entirety of the complementary region. This term is applied to pairs of polynucleotides based solely upon their sequences and not any particular set of conditions under which the two polynucleotides would actually bind.

The term "construct" as used herein refers to an artificially assembled or isolated nucleic acid molecule which includes the polynucleotide of interest. In general a construct may include the polynucleotide or polynucleotides of interest, a marker gene which in some cases can also be a gene of interest and appropriate regulatory sequences. It should be appreciated that the inclusion of regulatory sequences in a construct is optional, for example, such sequences may not be required in situations where the regulatory sequences of a host cell are to be used. The term construct includes vectors but should not be seen as being limited thereto.

The term "expression", as used herein, refers to the production of a functional end-product e.g., an mRNA or a protein.

The term "transgenic" when used in reference to an organism according to the teachings of the present invention (i.e., a "transgenic organism") refers to an organism that contains at least one heterologous transcribable polynucleotide in one or more of its cells. The term "transgenic material" refers broadly to a plant, algae, a cyanobacterium or part thereof, including cells or tissues that contain at least one heterologous polynucleotide in at least one cell.

The terms "transformants" or "transformed cells" include the primary transformed cell and cultures derived from that cell without regard to the number of transfers. All progeny may not be precisely identical in DNA content; however, all progeny that have the same functionality as in the originally transformed cell are included in the definition of transformants.

Transformation of a cell may be stable or transient. The term "transient transformation" or "transiently transformed" refers to the introduction of one or more exogenous polynucleotides into a cell in the absence of integration of the exogenous polynucleotide into the host cell's genome. In contrast, the term "stable transformation" or "stably transformed" refers to the introduction and integration of one or more exogenous polynucleotides into the genome of a cell. The term "stable transformant" refers to a cell which has stably integrated one or more exogenous polynucleotides into the genomic or organellar DNA. It is to be understood that an organism or its cell transformed with the nucleic acids, constructs and/or vectors of the present invention can be transiently as well as stably transformed.

Preferred modes for carrying out the invention

In the course of investigating the carotenoid biosynthesis pathway, particularly the desaturation and isomerizations steps that convert phytoene to trans-lycopene, the inventors of the present invention have used an isogenic tomato "mutation library" generated in the genetic background of the processing tomato inbred variety M82, by one of the inventors of the present invention and co-workers (Menda, N. et al. 2004. Plant J. 38:861-872). For generating the library, a total of 13,000 M2 families, derived from ethyl methanesulfonate (EMS) chemical treatment and fast-neutron mutagenesis of seeds, were phenotyped in field conditions. Based on the phenotypes, the families were categorized into a morphological catalog that included 15 primary and 48 secondary categories. More than 3000 mutations have been identified, some of which represent new alleles of previously described phenotypes from the monogenic mutant collection of The Tomato Genetics Resource Center (TGRC). Many mutations fall into more than a single category, and therefore have pleiotropic effects on plant growth. Mutants are searchable and accessed in the Solanaceae Genome Network (SGN) on a site called "The Genes That Make Tomatoes". Numerous mutations with altered colors of fruits or flowers have been identified (see, for example, Galpaz, N. et al. 2008. Plant J. 53:717-730).

The Tomato Mutant ZETA

Screening of ethyl methanesulfonate (EMS) mutagenized plants of the above-described library with altered colors of fruits or flowers revealed a hitherto not characterized recessive mutation in the tomato (*Solanum lycopersicum* cv M82), that was named ZETA. Fruit of plant bearing ZETA are yellow-orange instead of the typical red color. The present invention now discloses that instead of the red pigment lycopene, fruit of ZETA accumulate phytoene, phytofluene and 9,15,9'-tri-cis-zeta-carotene. Phytoene, phytofluene and 9,15,9'-tri-cis-zeta-carotene were also accumulated in etiolated cotyledons and flowers of plants carrying the ZETA mutation. Exposure of cotyledons and other developing leave to light reverses the phenotype to normal. Young leaves of ZETA are virescent but turn green as they develop. Without wishing to be bound by any specific theory or mechanism of action, photosynthetic activity may be involved in the correction of the lesions in chloroplasts.

The accumulation of phytoene, phytofluene and 9,15,9'-tri-cis-zeta-carotene indicate that in organisms carrying ZETA the carotenoid biosynthesis is impaired in the metabolism of zeta carotene towards downstream carotenoids in the carotenoid biosynthesis pathway. The present invention now shows that ZETA is not allelic to ZDS or CRTISO. Thus, this mutation reveals a novel function (enzyme) that is essential for ζ-carotene metabolism in plants and other carotenoid-producing organisms. As the mutation was found to be involved with zeta carotene isomerization, the gene was designated Ziso.

Figure 2:
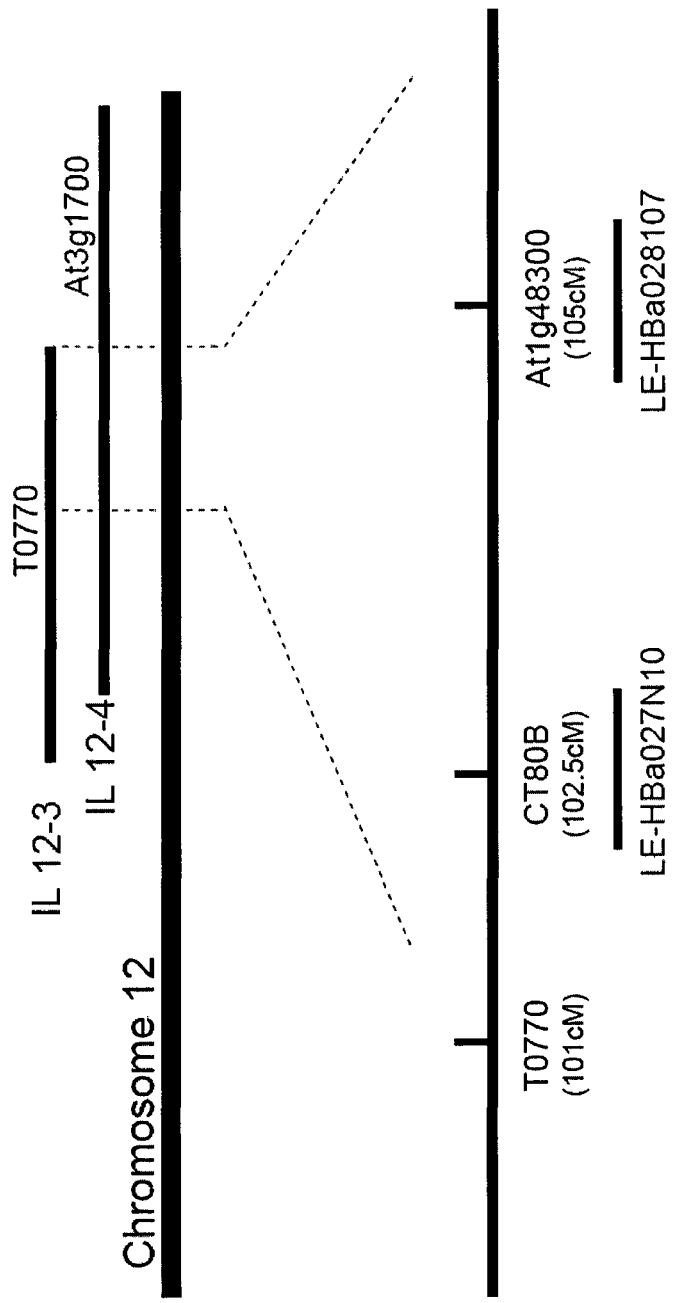
FIG. 2 is a schematic representation of the genetic map on chromosome #12 of tomato in the region near the locus ZETA. ZETA was located between markers CT80B and At1g48300. The BAC clones with tomato genomic sequences covering these markers are indicated.

The mutation ZETA in the tomato cultivar M82 was genetically mapped to chromosome 12 overlapping the *S. pennellii* chromosomal segment in the introgression line IL12-4. Fine genetic mapping was done by screening of about 3000 F2 plants of a cross between ZETA and IL12-4. The results indicated that the locus ZETA maps very close (<0.8 cM) to the genetic marker At1g48300 (FIG. 2).

Thus, according to one aspect, the present invention provides a genetically altered carotenoid-producing organism comprising at least one cell having reduced expression or activity of Ziso compared to a corresponding non-altered organism, wherein the genetically altered organism has an elevated content of at least one carotenoid selected from the group consisting of phytoene, phytofluene, zeta carotene and combinations thereof compared to the corresponding non-altered organism.

According to certain embodiments, the genetically altered organism comprises elevated content of phytoene compared to a corresponding non-altered organism. According to additional embodiments, the genetically altered organism comprises elevated content of phytofluene compared to a corresponding non-altered organism. According to yet further embodiments, the genetically altered organism comprises elevated content of a combination of phytoene and phytofluene compared to a corresponding non-altered organism.

According to certain embodiments, the cell having reduced expression or activity of Ziso is a chromoplast-containing cell. According to certain embodiments, the elevated content of at least one carotenoid of phytoene, phytofluene and zeta-carotene in the genetically altered organism is present in fleshy fruit tissues.

According to certain embodiments, the carotenoid-producing organism is selected from the group consisting of a plant, an alga and a cyanobacterium. According to typical embodiments, the organism is a plant.

According to certain embodiments, as exemplified hereinbelow, the native non-altered Ziso gene comprises a nucleic acid sequence at least 55%, typically at least 60%, 70%, 75%, more typically at least 80%, 85%, 95% and more homologous to the nucleic acid sequence set forth in SEQ ID NO:2. According to other embodiments, the Ziso gene comprises the nucleic acid sequence set forth in SEQ ID NO:2. Each possibility represents a separate embodiment of the present invention.

According to certain embodiments, as exemplified hereinbelow, the native unmodified Ziso protein of the organism comprises an amino acid sequence at least 55%, typically at least 60%, 70%, 75%, more typically at least 80%, 85%, 95% and more homologous to the amino acid sequence set forth in SEQ ID NO:3. According to typical embodiments, the unmodified Ziso protein comprises the amino acid sequence set forth in SEQ ID NO:3. Each possibility represents a separate embodiment of the present invention.

Any method as is known to a person skilled in art for down regulating the Ziso expression and/or activity can be used to produce the genetically altered organism of the present invention. According to certain embodiments, inhibiting Ziso expression can be affected at the genomic and/or the transcript level. According to other embodiments, expression can be inhibited at the protein level using, e.g., antagonists, enzymes that cleave the polypeptide, and the like.

According to certain embodiments, the genetically altered organism comprises a mutated Ziso gene.

Mutagenesis

Mutations can be introduced into the Ziso gene using, for example, site-directed mutagenesis (see, e.g. Zheng L. et al. 2004 Nucleic Acid Res. 10:32(14):e115. Such mutagenesis can be used to introduce a specific, desired amino acid insertion, deletion or substitution. Chemical mutagenesis using an agent such as Ethyl Methyl Sulfonate (EMS) can be employed to obtain a population of point mutations and screen for mutants of the Ziso gene that may become silent or down-regulated. In plants, methods relaying on introgression of genes from natural or mutated populations can be used. Cultured and wild types species are crossed repetitively such that a plant comprising a given segment of the wild or mutated genome is isolated. Certain plant species, for example Maize (corn) or snapdragon have natural transposons. These transposons are either autonomous, i.e. the transposas is located within the transposon sequence or non-autonomous, without a transposas. A skilled person can cause transposons to "jump" and create mutations. Alternatively, a nucleic acid sequence can be synthesized having random nucleotides at one or more predetermined positions to generate random amino acid substituting.

According to some embodiments, the mutated gene encodes a non-functional Ziso protein. According to certain typical embodiments, the mutated gene comprises the nucleic acids sequence set forth in SEQ ID NO:4 (designated ZETA$^{0089}$), encoding a non-functional Ziso protein having SEQ ID NO:5. According to additional typical embodiments the mutated gene comprises the nucleic acid sequence set forth in SEQ ID NO:6 (designated ZETA$^{2803}$) encoding a non-functional Ziso protein having SEQ ID NO:7.

According to additional embodiments, the genetically altered organism is a transgenic organism comprising at least one cell comprising a Ziso silencing molecule selected from the group consisting of RNA interference molecule, an antisense molecule and a ribozyme-encoding molecule.

RNA Interference (RNAi) Molecules

RNAi refers to the introduction of homologous double stranded RNA (dsRNA) to target a specific gene product, resulting in post transcriptional silencing of that gene. This phenomenon was first reported in *Caenorhabditis elegans* by Guo and Kemphues (1995. Cell, 81(4):611-620) and subsequently Fire et al. (1998. Nature 391:806-811) discovered that it is the presence of dsRNA, formed from the annealing of sense and antisense strands present in the in vitro RNA preparations, that is responsible for producing the interfering activity.

The present invention contemplates the use of RNA interference (RNAi) to down regulate the expression of Ziso to increase the level of phytoene, phytofluene and zeta-carotene in carotenoid-producing organisms. In both plants and animals, RNAi is mediated by RNA-induced silencing complex (RISC), a sequence-specific, multicomponent nuclease that destroys messenger RNAs homologous to the silencing trigger. RISC is known to contain short RNAs (approximately 22 nucleotides) derived from the double-stranded RNA trigger. The short-nucleotide RNA sequences are homologous to the target gene that is being suppressed. Thus, the short-nucleotide sequences appear to serve as guide sequences to instruct a multicomponent nuclease, RISC, to destroy the specific mRNAs.

The dsRNA used to initiate RNAi, may be isolated from native source or produced by known means, e.g., transcribed from DNA. Plasmids and vectors for generating RNAi molecules against target sequence are now readily available.

The dsRNA can be transcribed from the vectors as two separate strands. In other embodiments, the two strands of DNA used to form the dsRNA may belong to the same or two different duplexes in which they each form with a DNA strand of at least partially complementary sequence. When the dsRNA is thus-produced, the DNA sequence to be transcribed is flanked by two promoters, one controlling the transcription of one of the strands, and the other that of the complementary strand. These two promoters may be identical or different. Alternatively, a single promoter can derive the transcription of single-stranded hairpin polynucleotide having self-complementary sense and antisense regions that anneal to produce the dsRNA.

Inhibition is sequence-specific in that nucleotide sequences corresponding to the duplex region of the RNA are targeted for genetic inhibition. RNA molecules containing a nucleotide sequence identical to a portion of the target gene are preferred for inhibition. RNA sequences with insertions, deletions, and single point mutations relative to the target sequence have also been found to be effective for inhibition. Thus, sequence identity may be optimized by sequence comparison and alignment algorithms known in the art (see, e.g. Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript. The length of the identical nucleotide sequences may be at least 20, 25, 50, 100, 200, 300 or 400 bases. There is no upper limit on the length of the dsRNA that can be used. For example, the dsRNA can range from about 21 base pairs (bp) of the gene to the full length of the gene or more.

According to of double-stranded RNA molecule, comprising a first polynucleotide having a nucleic acid sequence having at least 90% sequence identity to a portion of the Ziso gene and a second polynucleotide having a nucleic acid sequence complementary to the first nucleic acid. According to certain embodiments, the Ziso gene is a tomato gene comprising the polynucleotide sequence set forth in SEQ ID NO:2. According to other embodiments, the Ziso gene is an ortholog of the tomato gene.

Antisense Molecules

Antisense technology is the process in which an antisense RNA or DNA molecule interacts with a target sense DNA or RNA strand. A sense strand is a 5' to 3' mRNA molecule or DNA molecule. The complementary strand, or mirror strand, to the sense is called an antisense. When an antisense strand interacts with a sense mRNA strand, the double helix is recognized as foreign to the cell and will be degraded, resulting in reduced or absent protein production. Although DNA is already a double stranded molecule, antisense technology can be applied to it, building a triplex formation.

RNA antisense strands can be either catalytic or non-catalytic. The catalytic antisense strands, also called ribozymes, cleave the RNA molecule at specific sequences. A non-catalytic RNA antisense strand blocks further RNA processing.

Antisense modulation of Ziso levels in cells and tissues may be effected by transforming the organism cells or tissues with at least one antisense compound, including antisense DNA, antisense RNA, a ribozyme, DNAzyme, a locked nucleic acid (LNA) and an aptamer. In some embodiments the molecules are chemically altered. In other embodiments the antisense molecule is antisense DNA or an antisense DNA analog. According to certain embodiments, the Ziso gene is a tomato gene comprising the polynucleotide sequence set forth in any one of SEQ ID NO:1 and SEQ ID NO:2. According to other embodiments, the Ziso gene is an ortholog of the tomato gene.

DNAzyme Molecules

Another agent capable of downregulating the expression of Ziso is a DNAzyme molecule, which is capable of specifically cleaving an mRNA transcript or a DNA sequence of the Ziso. DNAzymes are single-stranded polynucleotides that are capable of cleaving both single- and double-stranded target sequences. A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions (for review of DNAzymes, see: Khachigian, L. M. 2002. Curr Opin Mol Ther 4:119-121).

Examples of construction and amplification of synthetic, engineered DNAzymes recognizing single- and double-stranded target cleavage sites are disclosed in U.S. Pat. No. 6,326,174.

Enzymatic Oligonucleotide

The terms "enzymatic nucleic acid molecule" or "enzymatic oligonucleotide" refers to a nucleic acid molecule which has complementarity in a substrate binding region to a specified gene target, and also has an enzymatic activity which is active to specifically cleave target Ziso RNA, thereby silencing Ziso. The complementary regions allow sufficient hybridization of the enzymatic nucleic acid molecule to the target RNA and subsequent cleavage. The term enzymatic nucleic acid is used interchangeably with for example, ribozymes, catalytic RNA, enzymatic RNA, catalytic DNA, aptazyme or aptamer-binding ribozyme, catalytic oligonucleotide, nucleozyme, DNAzyme and RNAzyme. Any enzymatic nucleic acid molecules as is known in the art can be used according to the teachings of the present invention, as long as it has a specific substrate binding site which is complementary to one or more of the target nucleic acid regions, and that it has nucleotide sequences within or surrounding that substrate binding site which impart a nucleic acid cleaving and/or ligation activity to the molecule. U.S. Pat. No. 4,987,071 discloses examples of such molecules.

Transgenic Organisms

Cloning of a polynucleotide encoding a Ziso silencing molecule can be performed by any method as is known to a person skilled in the art. Various DNA constructs may be used to express the Ziso-targeted silencing molecule in a desired organism.

According to certain embodiments, the present invention provides an expression vector comprising all necessary elements for expression of the silencing molecule. According to certain embodiments, the expression of the silencing molecule is controlled by a constitutive promoter. According to currently typical embodiments, the organism is a plant, and the constitutive promoter is tissue specific. According to these embodiments, the specific promoter is selected from the group consisting of root specific promoter and fruit specific promoter. Root specific promoters are described, e.g. in Martinez, E. et al. 2003. Curr. Biol. 13:1435-1441. Fruit specific promoters are described among others in Estornell L. H et al. 2009. Plant Biotechnol. J. 7:298-309 and Fernandez A. I. Et al. 2009 Plant Physiol. 151:1729-1740.

According to certain embodiments, the expression vector further comprises regulatory elements at the 3' non-coding sequence. As used herein, the "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht I L et al. (1989. Plant Cell 1:671-680).

Those skilled in the art will appreciate that the various components of the nucleic acid sequences and the transformation vectors described in the present invention are operatively linked, so as to result in expression of said nucleic acid or nucleic acid fragment. Techniques for operatively linking the components of the constructs and vectors of the present invention are well known to those skilled in the art. Such techniques include the use of linkers, such as synthetic linkers, for example including one or more restriction enzyme sites.

Methods for transforming a carotenoid-producing organism selected from the group consisting of a plant, an alga and a cyanobacterium are known to those skilled in the art. As used herein the term "transformation" or "transforming" describes a process by which a foreign DNA, such as a DNA construct, including expression vector, enters and changes a recipient cell into a transformed, genetically altered or transgenic cell. Transformation may be stable, wherein the nucleic acid sequence is integrated into the organism genome and as such represents a stable and inherited trait, or transient, wherein the nucleic acid sequence is expressed by the cell transformed but is not integrated into the genome, and as such represents a transient trait. According to preferred embodiments the nucleic acid sequence of the present invention is stably transformed into the organism cell.

According to a further aspect, the present invention provides a method of elevating the content of at least one of phytoene, phytofluene, zeta carotene or combinations thereof in at least one cell of an organism, comprising inhibiting the Ziso expression in the at least one cell, thereby producing an organism having an elevated amount of phytoene, phytofluene, zeta carotene or combinations thereof in said at least one cell compared to a corresponding cell with non-inhibited Ziso expression.

According to certain embodiments, inhibiting the Ziso expression comprises introducing a mutation in the Ziso encoding gene, wherein the mutation results in reduced expression of the Ziso gene or in the production of non-functional Ziso protein. Any method for introducing a mutation in the Ziso gene as disclosed herein and as is known in the art can be used according to the teachings of the present invention.

According to some embodiments, inhibiting the Ziso expression comprises transforming at least one cell of the organism with a molecule designed to silence the expression of the Ziso gene, the gene having the nucleic acid sequence set forth in any one of SEQ ID NO:1, SEQ ID NO:2 or orthologs thereof. According to certain embodiments, the silencing molecule is selected from the group consisting of an antisense molecule, an RNAi molecule, a ribozyme encoding polynucleotide and the like.

The genetically altered organisms having elevated content of the desired carotenoid(s) according to the teachings of the present invention are typically first selected based on the expression of the Ziso gene or protein. Organisms having aberrant expression of Ziso are then analyzed for the content of phytoene, phytofluene, zeta- or combinations thereof.

Detection of mutated Ziso and/or the presence of Ziso silencing molecule and/or the presence of non-functional Ziso protein is performed employing standard methods of molecular genetic, known to a person of ordinary skill in the art.

For measuring the Ziso gene or silencing molecule expression, cDNA or mRNA should be obtained from an organ in which the nucleic acid is expressed. The sample may be further processed before the detecting step. For example, the polynucleotides in the cell or tissue sample may be separated from other components of the sample, may be amplified, etc. All samples obtained from an organism, including those subjected to any sort of further processing are considered to be obtained from the organism.

Detection of the Ziso gene or the silencing molecule typically requires amplification of the polynucleotides taken from the candidate altered organism. Methods for DNA amplification are known to a person skilled in the art. Most commonly used method for DNA amplification is PCR (polymerase chain reaction; see, for example, PCR Basics: from background to Bench, Springer Verlag, 2000; Eckert et al., 1991. PCR Methods and Applications 1:17). Additional suitable amplification methods include the ligase chain reaction (LCR), transcription amplification and self-sustained sequence replication, and nucleic acid based sequence amplification (NASBA).

According to certain embodiments, the nucleic acid sequence comprising the Ziso silencing molecule further comprises a nucleic acid sequence encoding a selectable marker. According to certain embodiments, the selectable marker confers resistance to antibiotic or, in case of plants and algae, to herbicide; in these embodiments the transgenic organisms are selected according to their resistance to the antibiotic or herbicide.

The total content of carotenoids as well as of each of phytoene, phytofluene and zeta-carotene is measured by standard methods known in the art (see, for example, Schiedt K and Liaaen-Jensen S. 1995. Carotenoids: Isolation and analysis. In Carotenoids Volume 1A: Isolation and Analysis, G. Britton, S. Liaaen-Jensen, and H. Pfander, Eds (Basel: Birkhauser), pp. 81-108).

According to certain embodiments, the genetically altered organism of the present invention has a phytoene content of at least 25% (w/w) of the total carotenoid content of the genetically altered cell. According to certain typical embodiments the phytoene content is at least 30%, more typically at least 35%, 40%, 45%, 50%, 55%, 60%, 65%, 70% or 75% of the total amount of carotenoids (w/w) of the genetically altered cells. Each possibility represents a separate embodiment of the present invention.

According to other embodiments, the genetically altered organism of the present invention has a phytofluene content of at least 15% (w/w) of the total carotenoid content. According to certain typical embodiments the phytofluene content is at least 20%, more typically at least 25%, 30%, 35%, 40%, 45%, 50%, 55%, 60%, 65%, 70% or 75% of the total amount of carotenoids (w/w) of the genetically altered cells. Each possibility represents a separate embodiment of the present invention.

According to yet additional embodiments, the genetically altered organism of the present invention has a combined level of phytoene and phytofluene of at least 30% (w/w) of the total carotenoid content. According to certain typical embodiments, the combined level of phytoene and phytofluene is at least 35%, 40%, 45%, 50%, 55%, 60%, 65%, 70%, 75%, 80%, 85% 90% or 95% of the total amount of carotenoids (w/w) of the genetically altered cells. Each possibility represents a separate embodiment of the present invention.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Materials and Methods

Nucleic Acid Isolation and Analysis
DNA Extraction from Plants

Genomic DNA was extracted from leaves as described (Bernatzky R. and Tanksley S. 1986. Plant Mol. Biol. Reporter 4:37-41). For sequencing of ZETA alleles, genomic DNA was prepared from 0.1-0.2 g of leaf tissue by the DNAzol®ES reagent according to the manufacturer's recommended protocol (Molecular Research Center, Inc., Cincinnati, Ohio, USA).

RNA Extraction from Plants and cDNA Production

Total RNA was extracted from 0.1 g of leaf tissues or 1.0 g of fruit tissue by using TRI-REAGENT according to the manufacturer's recommended protocol (Molecular Research Center, Inc., Cincinnati, Ohio, USA; purchased from Sigma). Reverse transcription of total RNA was carried out by using oligo-dT as a primer and the SUPERSCRIPT™ II RNase⁻ Reverse Transcriptase (GibcoBRL) or ImProm-II™ Reverse Transcription System kit (Promega) according to the manufacturer's directions.

Mutation Analysis

For cDNA templates the Taq polymerase DynaZyme™ II DNA polymerase (recombinant, FinnZymes Oy, Espo, Finland) was used. For genomic DNA the Taq polymerase HotStarTaq® (QIAGEN Group) was also used. Use was according to the manufactures recommended protocol.

The following pairs of primers were used to amplify the cDNA sequence of Ziso for each of the ZETA alleles:

```
                                  (Z1-forward, SEQ ID NO: 9))
    1) 5'-ACTTAGAGCT CACATAACCTTGTA-3'.

(Z1-reverse, SEQ ID NO: 10)
    2) 5'-TGTATGGAAACGAGTTATGTAACA-3'
```

PCR products were sequenced and differences from the wild type sequence were resolved.

DNA Sequence Analysis

The DNA sequence was determined with the ABI Prism 377 DNA Sequencer (Perkin Elmer) and processed with ABI sequence analysis software. Vector NTI Suit software (InforMax, North Bethesda, Md. USA) was used for sequence analysis.

Carotenoid Analysis

To minimize carotenoids degradation and isomerization, all manipulations were carried out under very dim light and, when possible, carotenoids samples were kept under anaerobic conditions, on ice or at −20° C.

Carotenoid Extraction from Fruits

Fruit pigments were extracted from 0.2-0.6 g of fresh tissue. The tissue was ground in 1 ml of acetone and the solvent was collected and filtered. The remainder tissue debris was ground again in 1 ml dichloromethane, the solvent was filtered and pooled with the acetone filtrate. The grinding and collecting of solvents were repeated until the tissue lost all its color. Pigments were extracted by partitioning the solvents mixture against equal volume of diethyl ether and 0.2 volume of 12% w/v NaCl/$H_2O$. Colored ether fraction (upper phase) was collected, dried under a stream of $N_2$ and the dried lipid extract was re-dissolved in 70 µl acetone for further analysis.

Carotenoid Extraction from Flowers

Flower pigments were extracted from petals or anthers of fresh single flowers. The tissues were ground in 1 ml acetone and the acetone was collected and filtered. This process was repeated until all pigments were extracted from the tissue. Acetone was dried under a stream of $N_2$ and the dried fraction was dissolved in 450 µl ethanol. 50 µl 60% KOH (w/v) was added and samples were incubated for 16 hours at 4° C. for saponification. The carotenoids were extracted by partitioning the mixtures against equal volume of diethyl ether and 0.2 volume of 12% w/v NaCl/$H_2O$. Upper phase (ether) was collected, dried under a stream of $N_2$ and the dried carotenoids were dissolved in acetone for further analysis.

Carotenoid Extraction from Cotyledons

Leaf pigments were extracted from 30-100 mg of fresh cotyledons (from 5-12 seedlings) of dark- or light-grown seedlings. Fresh tissue was minced in acetone and filtered. The solvent was dried under a stream of nitrogen and dissolved in 70 µl acetone for further analysis by HPLC.

High Performance Liquid Chromatography (HPLC) Analysis

Carotenoids were separated by High Performance Liquid Chromatography (HPLC) using a Waters system consisting of Waters 600 pump, Waters 996 photodiode array detector and Waters 717 plus Autosampler (Waters, Milford, Mass.). Two ODS2 C18 reversed-phase columns were used: one from Phenomenex (silica 5 µm, 3.2 mm×250 mm) (Phenomenex®, Torrance, Calif. USA) and one from Waters (5 µm, 4.6×250 mm) (Waters, Milford, Mass.). Both columns were coupled to a guard cartridge system SecurityGuard™ (Phenomenex®, Torrance, Calif. USA).

In HPLC system 1, which was used for preparative purposes, acetonitrile was used as the eluent at a constant flow rate of 1.6 ml/min (with the Waters column).

HPLC system 2, which was used for analytical purposes, was based on a gradient of solvents. Using acetonitrile:water (9:1; A) and ethylacetate (B), at a constant flow rate of 1 ml/min or 1.6 ml/min for the Phenomenex column or the Waters column, respectively. Gradient was: 100% to 80% A during 8 min; 80% to 65% A during 4 min, followed by 65% to 45% A during 14 min and a final segment at 100% B. Spectra at wave length range of 250-600 nm of eluting HPLC solvent was recorded and absorption peaks were detected. Carotenes were identified by their absorption spectra and retention time, and in some cases by comparison with authentic reference substances. Standards of all-trans-lycopene, all-trans-β-carotene and all-trans-neurosporene were obtained by carotenoids extraction from *E. coli* cells carrying plasmids pACCRT-EIB (Cunningham, F. X. Jr. et al. 1993. FEBS Lett. 328:130-138), pBCAR (Lotan, T. and Hirschberg, J. 1995. FEBS Lett. 364:125-128) and pAC-NEUR (Cunningham F. X. Jr. et al. 1994. Plant Cell 6:1107-1121). A standard of trans-ζ-carotene was purchased from CaroteNature GmbH (Lupsingen, Switzerland). Quantification was performed by integrating the peak areas using the Millennium chromatography software (Waters).

Carotenoid Quantification

Total carotenoid content was determined spectroscopically. For green tissues, quantification was preformed according to (Lichtenthaler, H. K. 1987. Methods Enzymol. 148:350-382). Pigments extracts were diluted 10 times in acetone and the absorbance of the samples was measured at 661.6 nm, 644.8 nm and 470 nm. Content of chlorophylls and total carotenoid were calculated as follows:

$$Chl_a \text{ (µg/mL acetone)} = 11.24 \times A_{661.6} - 2.04 \times A_{644.8}$$

$$Chl_b \text{ (µg/mL acetone)} = 20.13 \times A_{644.8} - 4.19 \times A_{661.6}$$

$$\text{Carotenoid (µg/mL acetone)} = (1000 \times A_{470} - 1.9 \times Chl_a - 63.14 \times Chl_b)/214$$

Where $A_x$ stands for the absorbance of 1 ml sample in a 1 cm path-length cuvette at the given (x) wave length.

For colored tissues, carotenoids quantification followed Schiedt and Liaaen-Jensen. (Schiedt K. and Liaaen-Jensen S. 1995. Carotenoids: Isolation and analysis. In Carotenoids Volume 1A: Isolation and Analysis, G. Britton, S. Liaaen-Jensen, and H. Pfander, Eds (Basel: Birkhauser), pp. 81-108.)

$$\text{Carotenoids (mg/mL)} = (A \times 1000)/(A_{1\,cm}^{1\%} \times 100)$$

Where A stands for the absorbance of 1 ml sample in a 1 cm path-length cuvette at a specific wave length (470 nm for xanthophylls or trans-lycopene, and 440 nm for prolycopene) and $A_{1\,cm}^{1\%}$ is the specific absorption coefficient (2400, 3400 or 1920 for xanthophylls, trans-lycopene or prolycopene, respectively) which is defined as the theoretical absorbance of a solution of 1% concentration in a 1 cm path-length cuvette.

Content of ζ-carotene, phytofluene and phytoene was calculated according to their relative proportion to xanthophylls, trans-lycopene or prolycopene in the tissue.

Example 1

Characterization of the ZETA Mutation

The mutation ZETA in the tomato cultivar M82 was genetically mapped to chromosome 12 overlapping the *S. pennellii* chromosomal segment in the introgression line IL12-4. Fine genetic mapping was done by screening of about 3000 F2 plants of a cross between ZETA and IL12-4. The results indicated that the locus ZETA maps very close (<0.8 cM) to the genetic marker At1g48300 (FIG. 2).

The gene encoding ZETA, named Ziso, was cloned based on homology to the *Arabidopsis* gene At1G10830, which had been identified by Dr. Elli Wurtzel (CUNY, Lehman College, personal communication). Complete co-segregation of the tomato ortholog of At1G10830 sequence and the ZETA mutation was established in F2 population of a cross ZETA×*S. pimpinellifolium*.

The DNA sequence of the wild type tomato gene Ziso comprises the nucleic acid sequence set forth in SEQ ID NO:1 (FIG. 3), and is transcribed to Ziso cDNA having the nucleic acid sequence set forth in SEQ ID NO:2 (FIG. 4).

The gene Ziso in tomato encodes a polypeptide of 369 amino acids with a calculated molecular weight of 41.5 kDa. A transit peptide sequence of 80 amino acids for plastid targeting is predicted by ChloroP program at the amino terminus. The size of the mature polypeptide is predicted to be 32.4 kDa and to contain five trans-membrane helices. Bioinformatic analysis revealed that Ziso occurs in all cyanobacteria, algae and plants. Its function has been annotated as "unknown" although a related motif exists in a bacterial gene Nnru.

Sequences analyses of two Zeta alleles: $z^{0089}$, having the nucleic acid sequence set forth in SEQ ID NO:4 (FIG. 5A); and $z^{2083}$, having the nucleic acids sequence set firth in SEQ ID NO:6 (FIG. 5B), revealed that each Zeta allele carries a unique nonsense mutation. The encoded proteins of the two alleles are non-functional, and have the amino acid sequences set forth in SEQ ID NO:5 and SEQ ID NO:7, respectively. Alignment of the amino acid sequences of ZISO polypeptides from wild type, $z^{2083}$ and $z^{0089}$ is presented in FIG. 5C.

The carotenoid composition in fruit and flowers of tomato plant carrying the ZETA mutation ($z^{2083}$) compared with the carotenoid composition of a wild type (M82) tomato plant is presented in Table 1 below. Carotenoid concentration is presented in μg per gram fresh weight (FW). The results clearly show that phytoene, phytofluene and zeta carotene content is significantly elevated in tomato plant carrying the ZETA mutation compared to a wild type plant.

TABLE 1

Carotenoid composition in fruit and flowers of wild type and ZETA tomato plants

| Carotenoid (μg/gFW) | Fruit | | Flowers | |
|---|---|---|---|---|
| | Wilt Type | ZETA ($Z^{2083}$) | Wilt Type | ZETA ($Z^{2083}$) |
| Phytoene | 7.6 | 28.5 | 0.1 | 44.3 |
| Phytofluene | 3.9 | 16.5 | Non-detectable | 15.5 |
| ζ-carotene | 0.7 | 38.0 | Non-detectable | 29.5 |
| β-carotene | 3.2 | 4.1 | <0.1 | <0.1 |
| Lycopene | 81.2 | 10.1 | <0.1 | <0.1 |
| Lutein | 3.0 | 2.8 | <0.1 | <0.1 |
| Violaxanthin | | | 30.5 | 5.7 |
| Neoxanthin | | | 65.9 | 3.2 |

Example 2

Breeding of Tomato Lines with High Phytoene and Phytofluene

Figure 6:
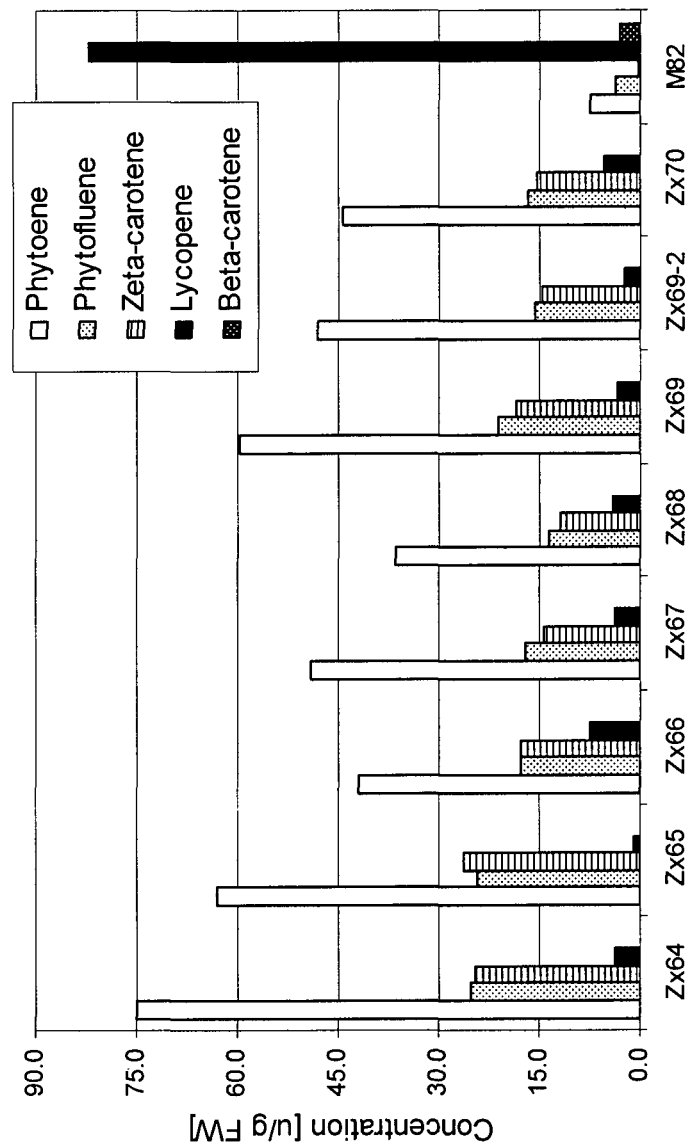
FIG. 6 shows the carotenoid composition in fruit of six F2 breeding lines carrying the mutation ZETA [μg/gr FW].

To increase the concentration of the desired phytoene and phytofluene (P&P) in tomato fruit, plant carrying the ZETA mutant $z^{0089}$, originated in the cultivar M82, were crossed with various breeding lines. Plants in F2 generation were grown in the field and fruit carotenoids were analyzed. Carotenoid composition was essentially similar to the original ZETA, namely, they contained high concentrations of phytoene, phytofluene and zeta-carotene, and very low amounts of lycopene (0.5 to 6 percent of total carotenoids) (FIG. 6). The average concentration of phytoene and phytofluene (P&P) in fruits in these lines was 70.8 μg/g fresh weight (FW), which corresponds to ca. 76 percent of total fruit carotenoids (Table 2). Plants carrying the ZETA mutation are designated "Z"; breeding lines are represented by numbers.

TABLE 2

Total carotenoid concentrations and ration of phytoene plus phytofluene in fruits of six F2 breeding lines carrying the ZETA mutation

| | Z × 64 | Z × 65 | Z × 66 | Z × 67 | Z × 68 | Z × 69 | Z × 69-2 | Z × 70 |
|---|---|---|---|---|---|---|---|---|
| Total Carotenoids (μg/gFW) | 128 ± 25 | 115 ± 34 | 86 ± 24 | 84 ± 28 | 67 ± 15 | 103 ± 23 | 81 ± 17 | 82 ± 27 |
| P&P (%) | 78 ± 4 | 76 ± 3.2 | 69 ± 5.6 | 78 ± 4.3 | 76 ± 15 | 77 ± 1.3 | 79 ± 2.7 | 74 ± 5 |

Example 3

Producing Algae with Increased P&P and Zeta-Carotene

Bioinformatic search in sequence databases revealed that genomes of algae and cyanobacteria (Blue-green algae) comprise genes that are similar to Ziso. For example, Synechococcus elongatus PCC7942 contains a gene, Synpcc7942_1979 annotated as "unknown function", with nucleotide sequence of 55.8% similarity to that of the tomato Ziso cDNA (SEQ ID NO:2). The amino acid sequence of Synpcc7942_1979 gene-product (protein ID AAG59994.1, SEQ ID NO:8) is 54% identical and 65.5% similar to the sequence of the tomato Ziso protein (SEQ ID NO:3).

We have deleted the gene Synpcc7942_1979 in a wild type strain of Synechococcus elongatus PCC7942 by means of transposon mutagenesis (Holtman, C. K. et al. 2005. DNA Res. 12:103-115). The mutated strain of S. elongatus PCC7942 was termed ΔZiso. Cells of this mutant grew slowly under low light intensity of 5-10 micromole photons per square meter per second. Analysis of total carotenoids in the mutant revealed that it accumulated tri-cis-zeta-carotene to a level of 6.5%, which is >500 folds higher than in the wild type (Table 3). This result indicates that Synpcc7942_1979 is a genuine Ziso ortholog. The results further confirm that, similarly to plants, mutations in Ziso cause accumulation of zeta-carotene in algae. Algae with mutated or silenced Ziso gene according to the teachings of the present invention are thus potential source for zeta-carotene and possibly also phytoene and phytofluene.

TABLE 3

Carotenoid composition (percent of total carotenoids)
in *Synechococcus elongatus* PCC7942 wild type and ΔZiso strains

|  | β-carotene | zeta-carotene | zeaxanthin | Others |
|---|---|---|---|---|
| Wild type | 57.5 | <0.01 | 36.5 | 6 |
| Δziso | 32.5 | 6.5 | 54.9 | 6.1 |

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A genetically altered tomato plant comprising at least one genetically altered chromoplast-containing fruit and/or flower cell having reduced expression or activity of a native Ziso protein compared to a corresponding non-altered chromoplast-containing fruit and/or flower cell, wherein:
   (i) the native Ziso protein comprises the amino acid sequence set forth in SEQ ID NO:3; and
   (ii) the at least one genetically altered chromoplast-containing fruit and/or flower cell comprises a polynucleotide comprising at least one mutation forming a mutated Ziso polynucleotide, wherein the at least one mutation results in reduced expression of the Ziso protein or in the production of a non-functional Ziso protein;
   said genetically altered fruit and/or flower cell comprises elevated content of at least one carotenoid selected from the group consisting of phytoene, phytofluene, zeta carotene and a combination thereof compared to the non-altered chromoplast-containing fruit and/or flower cell.

2. The genetically altered tomato plant of claim 1, wherein the native Ziso protein is encoded by a polynucleotide having the nucleic acid sequence set forth in SEQ ID NO:2.

3. The genetically altered tomato plant of claim 1, wherein the mutated Ziso polynucleotide comprises the nucleic acid sequence set forth in any one of SEQ ID NO:4 and SEQ ID NO:6.

4. The genetically altered tomato plant of claim 3, wherein the mutated Ziso polynucleotide encodes non-functional Ziso protein having the amino acid sequence set forth in any one of SEQ ID NO:5 and SEQ ID NO:7.

5. A seed of the genetically altered tomato plant of claim 1, wherein a plant grown from the seed comprises at least one genetically altered chromoplast-containing fruit and/or flower cell having a polynucleotide comprising at least one mutation forming a mutated Ziso polynucleotide, wherein the at least one mutation results in reduced expression of a native Ziso protein comprising the amino acid sequence set forth in SEQ ID NO:3 or in the production of a non-functional Ziso protein, thereby having elevated content of at least one carotenoid selected from the group consisting of phytoene, phytofluene, zeta-carotene and a combination thereof compared to a corresponding non-altered chromoplast-containing fruit and/or flower cell.

6. A cell suspension or tissue culture isolated from the genetically altered chromoplast-containing fruit and/or flower cell of the tomato plant of claim 1, wherein the tomato cell suspension or tissue culture comprise elevated content of at least one carotenoid selected from the group consisting of phytoene, phytofluene, zeta carotene and a combination thereof compared to a corresponding non-altered chromoplast-containing fruit and/or flower cell.

7. A method of elevating the content of phytoene, phytofluene, zeta carotene or a combination thereof in at least one chromoplast-containing fruit and/or flower cell of tomato plant, the method comprising inhibiting the expression or activity of a native Ziso protein having the amino acid sequence set forth in SEQ ID NO:3 in the at least one chromoplast-containing fruit and/or flower cell, wherein inhibiting the expression or activity of the Ziso protein comprises introducing a mutation in a polynucleotide encoding said Ziso protein thereby producing a plant having an elevated content of at least one carotenoid selected from the group consisting of phytoene, phytofluene, zeta carotene and a combination thereof in said at least one chromoplast-containing fruit and/or flower cell compared to a corresponding non-altered chromoplast-containing fruit and/or flower cell.

8. The method of claim 7, wherein the polynucleotide encoding the native Ziso protein comprises the nucleic acid sequence set forth in SEQ ID NO:2.

9. An isolated polynucleotide encoding non-functional Ziso protein having the amino acid sequence set forth in SEQ ID NO:5.

10. The isolated polynucleotide of claim 9, having the nucleic acid sequence set forth in SEQ ID NO:4.

11. An isolated polynucleotide encoding non-functional Ziso protein having the amino acid sequence set forth in SEQ ID NO:7.

12. The isolated polynucleotide of claim 11, having the nucleic acid sequence set forth in SEQ ID NO:6.

* * * * *

SEQUENCE LISTING

<160> NUMBER OF SEQ ID NOS: 10

<210> SEQ ID NO 1
<211> LENGTH: 8071
<212> TYPE: DNA
<213> ORGANISM: Solanum lycopersicum
<220> FEATURE:
<221> NAME/KEY: misc_feature
<222> LOCATION: (1752)..(1753)
<223> OTHER INFORMATION: n is a, c, g, or t

<400> SEQUENCE: 1

```
ccccaccgag caatctgtca agagagcaaa agcagagtta aaacgtgtac tggaggacat      60
taccatgcaa gcatcatcac ttcctggttc ggctcaacca ggcagatact cagttgtata     120
agaatgaaca ccgttgtcat tatgatgtta cttttatct attatctttt ccgagcaaat     180
tatttcctaa attttgttac tcaatttgga gatgacttac tttgtaatga tataaacagg     240
tttaactaga tacatgattc tcagtgatca tcggccatgg ttagttcctc tcctatatta     300
tctcatacct gttatctgta ttacttgatt cctttactga tagtatcatc aaagctgcta     360
tttgaattga aactgccaca gggagattac atagagttgc ccaggaagaa gcatggtatt     420
cagtcacccc gactaatatc ttgttaggaa agaaaccctg tggtaacttt tgtaacacaa     480
ttacttgaat ttcctattta ctcatgttat agagtagcag aattgcttga attctatgca     540
tgaggaatca tcatatgcac aaggttgatg acgattttca tgatggcatt gatccatata     600
cctaatggat cgtgagacga ctactagagc aaaggtatat tgactagatt cagtgttgtc     660
tttccatctt ctttgtggat ttggtagtaa atgaaaacag gtactgactt gactttttat     720
atttctaaaa tgttaaaaac tttacaagtt taaaatgtta aaccttctgc ttgtagattc     780
tcaagcaaca ctaacaaaaa aaaaaaaaaa aaaggaaaga aaatgtgaaa tgcctttggc     840
tctgtcttgt ccaatggatt ataagctttg gtttacttgc tataaagaga ctggaagcta     900
tctcaatgca tcgatacgtt gtttttgtt aagagtaccc actcctgaag actatataca     960
tcttcccctt acaggttagg cctgttgccg agaacgtggt aagaagttgt aaaaagaaaa    1020
gcatgtactg ttcagagtca tctagtgtca tttggttagt tggttaaact gaatttacat    1080
gctcaactcc cttgttttag attctactat ttatgtacta tttttctttg aggttgaacg    1140
gtatgtgtcg ttctgacttg ttctgctgtt ctcatattca tatccaagca atggaagaga    1200
atggtcacaa gaacaacctc ccaagttatg cttcacaaaa gcccctgtga aaacaacctt    1260
ccttttcaat ggtgtacatc ctagtgtata aatttgatgt taggtgtgtt attattctct    1320
tgctgtgaat ccaggtaaaa gtcattgtaa tttggtcagt cctcctctgc tggaaaagcc    1380
ttgtgctttc aatgcttggt agaatataga atcaagtgaa tagtgtatct tttcgatcaa    1440
tgttttgtgc ttgtaagttg aaaaaaaatg tacaatgagg ttttatattg tatccattta    1500
```

```
tgggattgta cttactattc acaacttagt tgatttgact cgactttcaa atcacttgta    1560
tcgtattcac gcggtttagt gattaatgaa atgaaaatag gttgataacg ataaatgtta    1620
gtattcacgc ggtttagtga ttaatgaaat gaaaataggt tgataacgat aaatgttagt    1680
gacgaataat tctaaaattg ctggcataca gtatcaccca acaaatggaa tatttacgac    1740
aaatcaattt tnnacttgat acaagtaaat ttttatcatt actttaaaag tgtatatata    1800
tatatatgat taggtaaaca ttattttgcc gacccaaacc aagaaaaaac aataaaatta    1860
gctacaagta gtgtatcatt tgcccacttt cctccactag ttatccaaaa tgcccaccaa    1920
agagcacaac tcctttaaga taccttttc cccttgccta ataaacttgt tttggtcaca     1980
gtttgtaaaa aaaaaaatta aatgttttg aataataaca taaaaaatta tttttttgaa     2040
aagatgaaaa aaataattc cttttaaaaa tacttgcaac aaataagatt tctcaaaata     2100 attttttta tgtcgtgtaa tttgattttc cacctcggaa tcctctttc tagttactct      2160 acccccaatt tttatttatt tgttgaaaaa aactaagaac ttggccaaga caggtttata    2220
tatttaccaa aactacacac ttagagctca cataatcttg taaaaatggc aacttcaatt    2280
tttctctcac accctttttc tcatttatta tcaaaacacc ataaaattcc aagtcctaaa    2340
caaaccatag ccatagcata tcactccacc aacaaaccca ccaccaagac tccatttta    2400 ccattaccca cttccttttt tccatttccc tcaaaccca gaaggaatt ttggccaatt      2460 tcagtgggaa gaacacaaac agatgaaaaa gatgaaatct tggtggtggg tgaagattct    2520
gctgaatttg agttatccaa acaaaagatt tcatcttggg tttatttgc tggggttctt     2580 ggtgttgtgc tttatgttct taatgttgtt tggattgaca attctactgg atttggaaaa    2640
tcattcattg attctgtttc tagtatttca gatagccctg aagtgagtat ttttgcttaa    2700 ttacttttc tgttctgttt ttatttactt ttgctgaatt gagttttgag gtattgcttt     2760
tgattatgtt cttacttgg taataatagt tgtataaatt gttagaacag taaaaaaatg     2820
atatcttttg tgaaaggtat aacgcataaa tatgtccttt aacttggcat atctgtgcct    2880
caaactttgg gcgtgcacac gttgatgctt aaacttgtat agagttaaaa catatgcatt    2940
ctatgtgtat gttaataata aagagaatt attactcact ttggtgttcc attattctat     3000
tttatgtttc ttaactttat tgtatagtga ttataaaatt tttgtagttt tctggaacgg    3060
gacggagttc ccacttcttc ctagcacatt tgctctcctt gtagcacttc tgacaaagat    3120
ttagttattt ttcatatgca tattttctta ttgtagtgtt ccagcacacc tttactattt    3180
taccggtttt acttattttc tcttaccgat ataggtttta ggtaactcta tccactaagc    3240
gttaggcaaa taggaagaga ttattaaacg cttctttgtt tttggccgct gtcgggattt    3300
aaaccctggt cttcattcta gtctaagtga acgctaactc acaccttgt gcgacatcac     3360 ccactgattg ttgtcttatg aatttgttta caatgaaata tggcttaaga cttttaagtt    3420
ctgctatcta ggcttagca tataattgag ccgaggttct attgggaaca acctccctat     3480
cctgcaaagg ttggggtaag gtgtgcatac atcgtaccct ctccagaatc cagaccctat    3540
gttgttgttg tagattagca tataaattaa aggtggcaac atcagtcatc ccgggcctct    3600
gtatattaaa aatcagggac tagtttaatc aatcagcact tggggattga gcttgtagga    3660
tcaagctttt aagcgttacg gagatgagaa aaagatagat aaaatctttt atctgcaaac    3720
tcccattcac aataattttg ttaattattt ttattgattt caatgttgtt attttcttct    3780
ttgtttgttt gtcacttggt gttagtcttg tgtagttact ttggttaatt caaacgaaat    3840
```

```
tatggaattg gtttacgttc aagacttttta caaggggaag cttttgttag catagtttta    3900
tcaaagaact ctatgagata ccaactaata gtcaaacaag aaccaacgaa ggagggtcga    3960
tttgaagttg ttaaccaaca aggttactta tgtttgggca actgtagaat aacattatgt    4020
cttcgccttg caatgaagac tatatagcct tgataatgct cggaaagtat ttatttgttc    4080
tggttcattc tgtcactctt cttggcttga taataggcaa gagatgcatt agattctcga    4140
tgaatatgca agagatgcat tagattctcg atgaatcata ttggccaaca taaaattgtc    4200
ttgatttctt tcctgttgtt tctttctttg tacacttagt tatttcacgt ccacttttgc    4260
catcttggta accagcatac actatataaa ttttttcattt cgcgtaccaa aatttctgct    4320
ttctgagagt ttatccaaat gtttctatgc agattgtaat gctttccctt accttgattt    4380
tcgctatagt ccacagtggt cttgctagtc ttagagacaa aggtgaggaa ctcattggag    4440
agcgtgcttt tcgtgtattg tttgctgggg tatctctgcc attggcagtc agcacaattg    4500
tgagttttct agtctgccat gcagaaacta agaattttgt ttattttttt gggtaacttt    4560
tctgatttta cggtgcgatg cttgatagat ggaaatttaa cataacgaaa ggttcttatg    4620
atgatttaca ggtgtatttc attaaccacc gatacgatgg agtgcagtta tggcaattaa    4680
acagtgttgc tgggattcac gaactagttt ggatttctaa ctttgtttcc ttcttcttcc    4740
tatacccgtc gacattcaat ttactagagg tagcggctgt tgacaagccc aagatgcatc    4800
tttgggaaac tgggattatg aggattacca ggcatccaca ggtaaatgct caattatcac    4860
ttaaatgtaa cctaccgttg tagaagatac agtctgaatg attttataat gtgccttgtc    4920
ccgaaacacc aatgcgtacc tttactttca aatctctttc caaattaaat ttcaacgttt    4980
gattcaaatc acttcgcttt gtacctcgta ttacatttta attccaggat atgacacttg    5040
ggagggtaga atgtacgtac gctgacctta ctcctacctt tgtggggtag agaggttgtc    5100
tccgatagac tctcaggtca aagaagtgt aatcaaagca gataagatag aagaaaaat    5160
aatgacaaca aaatactgag atatacagag caaatgaggc aacaggtgtt agaaaaagtt    5220
gaagaataag tactattaaa ggagaagatg agaagaggag actagccccc ttcctttccc    5280
acataaaaga acgacgacac tcgggtatct cataccctttc taccctaaac tgaccatata    5340
ccctcctacc taggattatg tcttcagcaa gctgaagatt agaccccgg ttcttctatt    5400
ttccaggata tgacgcaagt actatgacag aggaggttta gagtcatgat ttctaatcat    5460
tatttctgta gggttcagga attcttcttt tttaggtttt tcgtgtattt cagtcagata    5520
ctcaaaatta taaatcactt ttgattctta gaaccaagaa gtggatttat cggtcaatgg    5580
ttttctctga aggagttgaa taaggcatgt cacaaagaat gatatctcaa gaaatgacgg    5640
gcagaggttg atgcagaacg agtctgtaca tgaaatgagg tgaaggttat tgtaatccca    5700
gttctgctaa taatacataa aagggaagaa acctaccaaa ttgataaagc tgttccataa    5760
ttgaggattt tagtaaagag aaatcatctc aagtcctgaa aatcgagaaa ataagtgtct    5820
ttgtgcatat atgttacacg acagtccagt attcttgctt ctatttgctg tctcatttct    5880
tagtataagt tattccgtct ttgatagcta attgaagcct ccattcccta tattagctgg    5940
tcgggcaggt tatatggtgc ttagctcaca cgctgtggat tgggaattca gttgcagtgg    6000
cagcttcagt aggtttgata ggacatcatc tgtttggtgc ctggaatggg gaccggaggt    6060
tagccatacg atatggtgag gcttttgaag tcgtgaagaa cagaacgagt atcattccat    6120
ttgcagccat tcttgatggt cgtcaaaagt tgcctgaaga ttattacaag gaattttatca    6180
gattgccata tttatcgata acaacattga cattaggtgc ttacttcctc caccccatta    6240
```

```
tgcaagctgc cagttatcgg ctacactggt agtagtactg atgttacata actcgtttcc    6300
atacaagata tcgcgattac gagttgtata ttttcctca atatatatag gttactgatg    6360
tctatttaac tactgttgga taacaaagaa agaagaaga ggaatagaga gaattcagtt    6420
taatgtgttt gaaagtaaag ttccaacttg tatttccctt caatttctat atagtgtata    6480
tcatgacata tatgtccttg ttattccaat atatatatat atatggtacc aaagttttcg    6540
agtttgagtt atgttaatga attattattt tttataaaac gcgatttatc tctttagatg    6600
aacctcatgg tgtaaatttt gtttatttca tttagcggct tcaagtacca ataattaac     6660 taacggcatt atgtctgaat aaatgattca tcaaaataac gagttatcat taacattgag    6720
acatttgaaa tcgccaaata cgtaaaagtt tctcaaattt gattcatcta atgaacttca    6780
aatatcaagt aatttaaaaa atgatgcaaa tatcaataat tttatggtca gacaaggcct    6840
acctaaaagg agcaagtcag cttggaccaa atccaaaaat gaaaaaaaaa acagatttt     6900 ttttttttt ttataaatta aacactattc cacttctggt gttgaggaat tatcaaataa    6960
aagtacacca aattctttg acttttttt actttttgtg ataatgaaga aatacatgtg      7020
gccaatttga atgatatttt atatttaaat tcccttttgga tttactcttc ctcatgcaat   7080
gtgattggaa gagtagggaa tgagtaggtt cacttaagaa tgctacactt aaaccaatct    7140
gaataaattt ttcactcgat atttaatact aatcttaaag tcttattaaa tttaaattcg    7200
tatcgaaaaa tttcacatta aataataaga catttcccaa taagataact tcatgtccac    7260
gattcgaact caaaatccta attattatcc acatacatat acttctagga accttttaa     7320 cgtggcatac atacatcact cacttaaaaa gaacatacaa gttatatgtc actataaata    7380
aattattaca taacgataac tatttcatca ttcttaatca gaaaaaatta tattcacgct    7440
tttggtataa aatcggtttt gataagtaac gctttacccc tacaaagtga aactgtatat    7500
tgatcgaagt ccaaaataaa tatcgaaaaa taatacaacc gtgtataaaa ctatgtaaac    7560 ccccaccct ccacatacac acaaacactt catgggggtg gaggatttgg ttagtgtgct     7620 tttgtttta tttcataaaa attggactaa cattgggttg agttgcacag tttaaccaac     7680
tatattatat ccactttatt aagtttctaa cccactccat cattttaat atttctaatt     7740 taatgccaca ttgccaccaa cctactttaa tattgggtat gtcttacatt ttctataact    7800
aaaatcatac taacttctta tttaagccaa ttgcttaaca catctcatta ttattattat    7860
aactcttctt tctatttata taaatctttg tgatttatat gctattataa ttcactattg    7920
atttcatatt tcatatgcta attggaagaa atatgaagga aaaatcagta gagaaatttt    7980
tcatgttgcc attctatta gggtgtaatt ctgagtcaag tgttggagtg acaaaccaac     8040
ttgtggaaac aaagaattca tcacaaataa c                                   8071

<210> SEQ ID NO 2
<211> LENGTH: 1599
<212> TYPE: DNA
<213> ORGANISM: Solanum lycopersicum

<400> SEQUENCE: 2
tgaataataa cataaaaaat tattttttg aaaagatgaa aaaataatt tccttttaaa        60 aatacttgca acaaataaaa tttctcaaaa taatttttt tatgtcgggt aatttgattt      120
tccacctcgg aatcctcttt tctagttact ctaccccaa ttttattta tttgttgaaa      180 aaaactaaaa acttggccaa gacaggttta tatatttacc aaaactacac acttagagct     240
```

-continued

| | |
|---|---|
| cacataacct tgtaaaaatg caacttcaa tttttctctc acacccttt tctcatttat | 300 |
| tatcaaaaca ccataaaatt ccaagtccta aacaaaccat agccatagca tatcactcca | 360 |
| ccaacaaacc caccaccaag actccatttt taccattacc cacttccttt tttccatttc | 420 |
| cctcaaaccc cagaaaggaa ttttggccaa tttcagtggg aagaacacaa acagatgaaa | 480 |
| aagatgaaat cttggtggtg ggtgaagatt ctgctgaatt tgagttatcc aaacaaaaga | 540 |
| tttcatcttg ggtttatttt gctggggttc ttggtgttgt gctttatgtt cttaatgttg | 600 |
| tttggattga caattctact ggatttggaa atcattcat tgattctgtt tctagtattt | 660 |
| cagatagccc tgaaattgta atgctttccc ttaccttgat tttcgctata gtccacagtg | 720 |
| gtcttgctag tcttagagac aaaggtgagg aactcattgg agagcgtgct tttcgtgtat | 780 |
| tgtttgctgg ggtatctctg ccattggcag tcagcacaat tgtgtatttc attaaccacc | 840 |
| gatacgatgg agtgcagtta tggcaattaa acagtgttgc tgggattcac gaactagttt | 900 |
| ggatttctaa ctttgtttcc ttcttcttcc tatacccgtc gacattcaat ttactagagg | 960 |
| tagcggctgt tgacaagccc aagatgcatc tttgggaaac tgggattatg aggattacca | 1020 |
| ggcatccaca gctggtcggg caggttatat ggtgcttagc tcacgcgctg tggattggga | 1080 |
| attcagttgc agtggcagct tcagtaggtt tgataggaca tcatctgttt ggtgcctgga | 1140 |
| atggggaccg gaggttagcc atacgatatg gtgaggcttt tgaagtcgtg aagaacagaa | 1200 |
| cgagtatcat tccatttgca gccattcttg atggtcgtca aaagttgcct gaagattatt | 1260 |
| acaaggaatt tatcagattg ccatatttat cgataacaac attgacatta ggtgcttact | 1320 |
| tcctccaccc cattatgcaa gctgccagtt atcggctaca ctggtagtag tactgatgtt | 1380 |
| acataactcg tttccataca agatatcgcg attacgagtt gtatatttt cctcaatata | 1440 |
| tataggttac tgatgtctat ttaactactg ttggataaca aagaaagaaa gaagaggaat | 1500 |
| agagagaatt cagtttaatg tgtttgaaag taaagttcca acttgtattt cccttcaatt | 1560 |
| tctatatagt gtatatcatg acatatatgt ccttgttat | 1599 |

<210> SEQ ID NO 3
<211> LENGTH: 369
<212> TYPE: PRT
<213> ORGANISM: Solanum lycopersicum

<400> SEQUENCE: 3

Met Ala Thr Ser Ile Phe Leu Ser His Pro Phe Ser His Leu Leu Ser
1               5                   10                  15

Lys His His Lys Ile Pro Ser Pro Lys Gln Thr Ile Ala Ile Ala Tyr
            20                  25                  30

His Ser Thr Asn Lys Pro Thr Thr Lys Thr Pro Phe Leu Pro Leu Pro
        35                  40                  45

Thr Ser Phe Phe Pro Phe Pro Ser Asn Pro Arg Lys Glu Phe Trp Pro
    50                  55                  60

Ile Ser Val Gly Arg Thr Gln Thr Asp Glu Lys Asp Glu Ile Leu Val
65                  70                  75                  80

Val Gly Glu Asp Ser Ala Glu Phe Glu Leu Ser Lys Gln Lys Ile Ser
                85                  90                  95

Ser Trp Val Tyr Phe Ala Gly Val Leu Gly Val Leu Tyr Val Leu
                100                 105                 110

Asn Val Val Trp Ile Asp Asn Ser Thr Gly Phe Gly Lys Ser Phe Ile
            115                 120                 125

Asp Ser Val Ser Ser Ile Ser Asp Ser Pro Glu Ile Val Met Leu Ser

```
                130             135             140
Leu Thr Leu Ile Phe Ala Ile Val His Ser Gly Leu Ala Ser Leu Arg
145                 150                 155                 160

Asp Lys Gly Glu Glu Leu Ile Gly Glu Arg Ala Phe Arg Val Leu Phe
                165                 170                 175

Ala Gly Val Ser Leu Pro Leu Ala Val Ser Thr Ile Val Tyr Phe Ile
            180                 185                 190

Asn His Arg Tyr Asp Gly Val Gln Leu Trp Gln Leu Asn Ser Val Ala
        195                 200                 205

Gly Ile His Glu Leu Val Trp Ile Ser Asn Phe Val Ser Phe Phe
    210                 215                 220

Leu Tyr Pro Ser Thr Phe Asn Leu Leu Glu Val Ala Ala Val Asp Lys
225                 230                 235                 240

Pro Lys Met His Leu Trp Glu Thr Gly Ile Met Arg Ile Thr Arg His
                245                 250                 255

Pro Gln Leu Val Gly Gln Val Ile Trp Cys Leu Ala His Thr Leu Trp
            260                 265                 270

Ile Gly Asn Ser Val Ala Val Ala Ala Ser Val Gly Leu Ile Gly His
        275                 280                 285

His Leu Phe Gly Ala Trp Asn Gly Asp Arg Arg Leu Ala Ile Arg Tyr
    290                 295                 300

Gly Glu Ala Phe Glu Val Val Lys Asn Arg Thr Ser Ile Ile Pro Phe
305                 310                 315                 320

Ala Ala Ile Leu Asp Gly Arg Gln Lys Leu Pro Glu Asp Tyr Tyr Lys
                325                 330                 335

Glu Phe Ile Arg Leu Pro Tyr Leu Ser Ile Thr Thr Leu Thr Leu Gly
            340                 345                 350

Ala Tyr Phe Leu His Pro Ile Met Gln Ala Ala Ser Tyr Arg Leu His
        355                 360                 365

Trp

<210> SEQ ID NO 4
<211> LENGTH: 1599
<212> TYPE: DNA
<213> ORGANISM: Artificial Sequence
<220> FEATURE:
<223> OTHER INFORMATION: Tomato ZETA mutant

<400> SEQUENCE: 4
tgaataataa cataaaaaat tattttttg aaagatgaa aaaataatt tccttttaaa      60 aatacttgca acaaataaaa tttctcaaaa taattttttt tatgtcgggt aatttgattt   120
tccacctcgg aatcctcttt tctagttact ctacccccaa ttttatttta tttgttgaaa   180
aaaactaaaa acttggccaa gacaggttta tatatttacc aaaactacac acttagagct   240 cacataaccct tgtaaaaatg gcaacttcaa tttttctctc acacccttt tctcatttat    300 tatcaaaaca ccataaaatt ccaagtccta aacaaaccat agccatagca tatcactcca   360
ccaacaaacc caccaccaag actccatttt taccattacc cacttccttt tttccatttc   420
cctcaaaccc cagaaaggaa ttttggccaa tttcagtggg aagaacacaa acagatgaaa   480
aagatgaaat cttggtggtg ggtgaagatt ctgctgaatt tgagttatcc aaacaaaaga   540
tttcatcttg ggtttatttt gctggggttc ttggtgttgt gctttatgtt cttaatgttg   600
tttggattga caattctact ggatttggaa aatcattcat tgattctgtt tctagtattt   660
cagatagccc tgaaattgta atgctttccc ttaccttgat tttcgctata gtccacagtg   720
```

```
gtcttgctag tcttagagac aaaggtgagg aactcattgg agagcgtgct tttcgtgtat      780
tgtttgctgg ggtatctctg ccattggcag tcagcacaat tgtgtatttc attaaccacc      840
gatacgatgg agtgcagtta tggcaattaa acagtgttgc tgggattcac gaactagttt      900
ggatttctaa ctttgtttcc ttcttcttcc tatacccgtc gacattcaat ttactagagg      960
tagcggctgt tgacaagccc aagatgcatc tttgggaaac tgggattatg aggattacca     1020
ggcatccaca gctggtcggg caggttatat ggtgcttagc tcacacgctg tggattggga     1080
attcagttgc agtggcagct tcagtaggtt tgataggaca tcatctgttt ggtgcctaga     1140
atggggaccg gaggttagcc atacgatatg gtgaggcttt tgaagtcgtg aagaacagaa     1200
cgagtatcat tccatttgca gccattcttg atggtcgtca aaagttgcct gaagattatt     1260
acaaggaatt tatcagattg ccatatttat cgataacaac attgacatta ggtgcttact     1320
tcctccaccc cattatgcaa gctgccagtt atcggctaca ctggtagtag tactgatgtt     1380
acataactcg tttccataca agatatcgcg attacgagtt gtatattttt cctcaatata     1440
tataggttac tgatgtctat ttaactactg ttggataaca aagaaagaaa gaagaggaat     1500
agagagaatt cagtttaatg tgtttgaaag taaagttcca acttgtattt cccttcaatt     1560
tctatatagt gtatatcatg acatatatgt ccttgttat                            1599

<210> SEQ ID NO 5
<211> LENGTH: 293
<212> TYPE: PRT
<213> ORGANISM: Artificial Sequence
<220> FEATURE:
<223> OTHER INFORMATION: Tomato ZETA mutant

<400> SEQUENCE: 5

Met Ala Thr Ser Ile Phe Leu Ser His Pro Phe Ser His Leu Leu Ser
1               5                   10                  15

Lys His His Lys Ile Pro Ser Pro Lys Gln Thr Ile Ala Ile Ala Tyr
            20                  25                  30

His Ser Thr Asn Lys Pro Thr Thr Lys Thr Pro Phe Leu Pro Leu Pro
        35                  40                  45

Thr Ser Phe Phe Pro Phe Pro Ser Asn Pro Arg Lys Glu Phe Trp Pro
    50                  55                  60

Ile Ser Val Gly Arg Thr Gln Thr Asp Glu Lys Asp Glu Ile Leu Val
65                  70                  75                  80

Val Gly Glu Asp Ser Ala Glu Phe Glu Leu Ser Lys Gln Lys Ile Ser
                85                  90                  95

Ser Trp Val Tyr Phe Ala Gly Val Leu Gly Val Leu Tyr Val Leu
                100                 105                 110

Asn Val Val Trp Ile Asp Asn Ser Thr Gly Phe Gly Lys Ser Phe Ile
            115                 120                 125

Asp Ser Val Ser Ser Ile Ser Asp Ser Pro Glu Ile Val Met Leu Ser
        130                 135                 140

Leu Thr Leu Ile Phe Ala Ile Val His Ser Gly Leu Ala Ser Leu Arg
145                 150                 155                 160

Asp Lys Gly Glu Glu Leu Ile Gly Glu Arg Ala Phe Arg Val Leu Phe
                165                 170                 175

Ala Gly Val Ser Leu Pro Leu Ala Val Ser Thr Ile Val Tyr Phe Ile
            180                 185                 190

Asn His Arg Tyr Asp Gly Val Gln Leu Trp Gln Leu Asn Ser Val Ala
        195                 200                 205
```

Gly Ile His Glu Leu Val Trp Ile Ser Asn Phe Val Ser Phe Phe
    210                 215                 220

Leu Tyr Pro Ser Thr Phe Asn Leu Leu Glu Val Ala Ala Val Asp Lys
225                 230                 235                 240

Pro Lys Met His Leu Trp Glu Thr Gly Ile Met Arg Ile Thr Arg His
                245                 250                 255

Pro Gln Leu Val Gly Gln Val Ile Trp Cys Leu Ala His Thr Leu Trp
            260                 265                 270

Ile Gly Asn Ser Val Ala Val Ala Ser Val Gly Leu Ile Gly His
        275                 280                 285

His Leu Phe Gly Ala
    290

<210> SEQ ID NO 6
<211> LENGTH: 1599
<212> TYPE: DNA
<213> ORGANISM: Artificial Sequence
<220> FEATURE:
<223> OTHER INFORMATION: Tomato ZETA mutant

<400> SEQUENCE: 6
tgaataataa cataaaaaat tatttttttg aaaagatgaa aaaataatt tccttttaaa      60 aatacttgca acaaataaaa tttctcaaaa taattttttt tatgtcgggt aatttgattt    120
tccacctcgg aatcctcttt tctagttact ctaccccca tttttattta tttgttgaaa    180
aaaactaaaa acttggccaa gacaggttta tatatttacc aaaactacac acttagagct    240
cacataacct tgtaaaaatg gcaacttcaa ttttctctc acccctttt tctcatttat     300 tatcaaaaca ccataaaatt ccaagtccta acaaaccat agccatagca tatcactcca     360
ccaacaaacc caccaccaag actccatttt taccattacc cacttccttt tttccatttc    420
cctcaaaccc cagaaaggaa ttttggccaa tttcagtggg aagaacacaa acagatgaaa    480
aagatgaaat cttggtggtg ggtgaagatt ctgctgaatt tgagttatcc aaacaaaaga    540
tttcatcttg ggtttatttt gctggggttc ttggtgttgt gctttatgtt cttaatgttg    600
tttggattga caattctact ggatttggaa atcattcat tgattctgtt tctagtattt     660
cagatagccc tgaaattgta atgctttccc ttaccttgat tttcgctata gtccacagtg    720
gtcttgctag tcttagagac aaaggtgagg aactcattgg agagcgtgct tttcgtgtat    780
tgtttgctgg ggtatctctg ccattggcag tcagcacaat tgtgtatttc attaaccacc    840
gatacgatgg agtgcagtta tggcaattaa acagtgttgc tgggattcac gaactagttt    900
ggatttctaa ctttgtttcc ttcttcttcc tatacccgtc gacattcaat ttactagagg    960
tagcggctgt tgacaagccc aagatgcatc tttaggaaac tgggattatg aggattacca   1020
ggcatccaca gctggtcggg caggttatat ggtgcttagc tcacacgctg tggattggga   1080
attcagttgc agtggcagct tcagtaggtt tgataggaca tcatctgttt ggtgcctaga   1140
atggggaccg gaggttagcc atacgatatg gtgaggcttt tgaagtcgtg aagaacagaa   1200
cgagtatcat tccatttgca gccattcttg atggtcgtca aaagttgcct gaagattatt   1260
acaaggaatt tatcagattg ccatatttat cgataacaac attgacatta ggtgcttact   1320
tcctccaccc cattatgcaa gctgccagtt atcggctaca ctggtagtag tactgatgtt   1380
acataactcg tttccataca agatatcgcg attacgagtt gtatattttt cctcaatata   1440
tataggttac tgatgtctat ttaactactg ttggataaca aagaaagaaa gaagaggaat   1500

```
agagagaatt cagtttaatg tgtttgaaag taaagttcca acttgtattt ccettcaatt   1560 tctatatagt gtatatcatg acatatatgt ccttgttat                          1599
```

<210> SEQ ID NO 7
<211> LENGTH: 245
<212> TYPE: PRT
<213> ORGANISM: Artificial Sequence
<220> FEATURE:
<223> OTHER INFORMATION: Tomato ZETA mutant

<400> SEQUENCE: 7

```
Met Ala Thr Ser Ile Phe Leu Ser His Pro Phe Ser His Leu Leu Ser
1               5                   10                  15

Lys His His Lys Ile Pro Ser Pro Lys Gln Thr Ile Ala Ile Ala Tyr
            20                  25                  30

His Ser Thr Asn Lys Pro Thr Thr Lys Thr Pro Phe Leu Pro Leu Pro
        35                  40                  45

Thr Ser Phe Phe Pro Phe Pro Ser Asn Pro Arg Lys Glu Phe Trp Pro
    50                  55                  60

Ile Ser Val Gly Arg Thr Gln Thr Asp Glu Lys Asp Glu Ile Leu Val
65                  70                  75                  80

Val Gly Glu Asp Ser Ala Glu Phe Glu Leu Ser Lys Gln Lys Ile Ser
                85                  90                  95

Ser Trp Val Tyr Phe Ala Gly Val Leu Gly Val Val Leu Tyr Val Leu
            100                 105                 110

Asn Val Val Trp Ile Asp Asn Ser Thr Gly Phe Gly Lys Ser Phe Ile
        115                 120                 125

Asp Ser Val Ser Ser Ile Ser Asp Ser Pro Glu Ile Val Met Leu Ser
    130                 135                 140

Leu Thr Leu Ile Phe Ala Ile Val His Ser Gly Leu Ala Ser Leu Arg
145                 150                 155                 160

Asp Lys Gly Glu Glu Leu Ile Gly Glu Arg Ala Phe Arg Val Leu Phe
                165                 170                 175

Ala Gly Val Ser Leu Pro Leu Ala Val Ser Thr Ile Val Tyr Phe Ile
            180                 185                 190

Asn His Arg Tyr Asp Gly Val Gln Leu Trp Gln Leu Asn Ser Val Ala
        195                 200                 205

Gly Ile His Glu Leu Val Trp Ile Ser Asn Phe Val Ser Phe Phe Phe
    210                 215                 220

Leu Tyr Pro Ser Thr Phe Asn Leu Leu Glu Val Ala Ala Val Asp Lys
225                 230                 235                 240

Pro Lys Met His Leu
                245
```

<210> SEQ ID NO 8
<211> LENGTH: 240
<212> TYPE: PRT
<213> ORGANISM: Synechococcus elungatus

<400> SEQUENCE: 8

```
Met Pro Leu Ser Trp Trp Thr Pro Ser His Thr Ile Met Leu Ala Leu
1               5                   10                  15

Leu Leu Leu Phe Ala Ile Ala His Ser Gly Leu Ala Ala Leu Arg Pro
            20                  25                  30

Trp Gly Glu Thr Lys Ile Gly Ala Arg Gly Tyr Arg Ile Leu Phe Ala
        35                  40                  45
```

```
Leu Val Ser Leu Pro Leu Ala Val Val Thr Ile Ser Tyr Phe Ile Leu
    50                  55                  60

His Arg Tyr Asp Gly Ala Leu Leu Trp Gln Leu Gln Gly Ile Pro Trp
 65              70                  75                  80

Ile Ala Pro Leu Val Trp Val Leu Thr Ala Ile Ser Phe Leu Leu Leu
                 85                  90                  95

Tyr Pro Ala Thr Phe Asn Leu Leu Glu Ile Ala Ala Ile Ala Gln Pro
            100                 105                 110

Gln Val Arg Leu Tyr Glu Thr Gly Ile Thr Arg Ile Thr Arg His Pro
            115                 120                 125

Gln Thr Phe Gly Gln Ile Leu Trp Cys Leu Ala His Ser Leu Trp Leu
130                 135                 140

Gly Thr Ser Phe Met Met Val Ala Ser Ala Gly Leu Ile Ala His His
145                 150                 155                 160

Leu Phe Ser Ile Trp His Gly Asp Arg Arg Leu Gln Lys Arg Tyr Gly
                165                 170                 175

Glu Ala Phe Glu Ala Leu Lys Ser Arg Thr Ser Ile Ile Pro Phe Leu
            180                 185                 190

Ala Ile Ala Gln Gly Lys Gln Thr Leu Val Trp Lys Glu Phe Leu Arg
            195                 200                 205

Pro Ala Tyr Leu Gly Val Ala Ile Ala Ile Gly Leu Phe Trp Phe Ala
        210                 215                 220

His Arg Trp Ile Pro Gln Ala Thr Ala Ala Leu Ala Glu Ile Gly Trp
225                 230                 235                 240

<210> SEQ ID NO 9
<211> LENGTH: 24
<212> TYPE: DNA
<213> ORGANISM: Artificial sequence
<220> FEATURE:
<223> OTHER INFORMATION: Primer

<400> SEQUENCE: 9
acttagagct cacataacct tgta                                          24

<210> SEQ ID NO 10
<211> LENGTH: 24
<212> TYPE: DNA
<213> ORGANISM: Artificial Sequence
<220> FEATURE:
<223> OTHER INFORMATION: Primer

<400> SEQUENCE: 10
tgtatggaaa cgagttatgt aaca                                          24
```